US008348885B2

(12) United States Patent
Moberg et al.

(10) Patent No.: US 8,348,885 B2
(45) Date of Patent: Jan. 8, 2013

(54) REMOTE MONITORING FOR NETWORKED FLUID INFUSION SYSTEMS

(75) Inventors: Sheldon B. Moberg, Thousand Oaks, CA (US); Kenny J. Long, Simi Valley, CA (US); Kaezad J. Mehta, Chatsworth, CA (US); Ian B. Hanson, Northridge, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 13/076,229

(22) Filed: Mar. 30, 2011

(65) Prior Publication Data

US 2011/0178462 A1 Jul. 21, 2011

Related U.S. Application Data

(62) Division of application No. 11/414,160, filed on Apr. 28, 2006, now Pat. No. 7,942,844.

(51) Int. Cl.
*A61M 31/00* (2006.01)
(52) U.S. Cl. .......................................................... 604/65
(58) Field of Classification Search ............... 604/890.1, 604/65–67, 131; 128/DIG. 12, DIG. 13
See application file for complete search history.

(56) References Cited

U.S. PATENT DOCUMENTS

| 5,704,351 A | 1/1998 | Mortara et al. |
| 5,781,442 A * | 7/1998 | Engleson et al. ............. 700/214 |
| 6,154,675 A | 11/2000 | Juran et al. |
| 6,402,691 B1 | 6/2002 | Peddicord et al. |
| 6,551,276 B1 * | 4/2003 | Mann et al. ................... 604/131 |
| 6,558,321 B1 | 5/2003 | Burd et al. |
| 6,564,104 B2 | 5/2003 | Nelson et al. |
| 6,675,030 B2 | 1/2004 | Ciurczak et al. |
| 7,450,511 B2 | 11/2008 | Jang |
| 7,813,324 B1 | 10/2010 | Goel et al. |
| 2001/0023189 A1 | 9/2001 | Kajimura |
| 2002/0089959 A1 | 7/2002 | Fischer et al. |
| 2005/0010093 A1 | 1/2005 | Ford et al. |
| 2006/0026296 A1 | 2/2006 | Nagaraj |
| 2006/0062243 A1 | 3/2006 | Dacosta |
| 2007/0233521 A1 | 10/2007 | Wehba et al. |

* cited by examiner

Primary Examiner — Manuel Mendez
(74) Attorney, Agent, or Firm — Ingrassia Fisher & Lorenz, P.C.

(57) ABSTRACT

A fluid infusion system as described herein includes a number of local "body network" devices, such as an infusion pump, a handheld monitor or controller, a physiological sensor, and a bedside or hospital monitor. The body network devices can be configured to support communication of status data, physiological information, alerts, control signals, and other information between one another. In addition, the body network devices can be configured to support networked communication of status data, physiological information, alerts, control signals, and other information between the body network devices and "external" devices, systems, or communication networks. Such external communication allows the infusion system to be extended beyond the traditional short-range user environment.

15 Claims, 13 Drawing Sheets

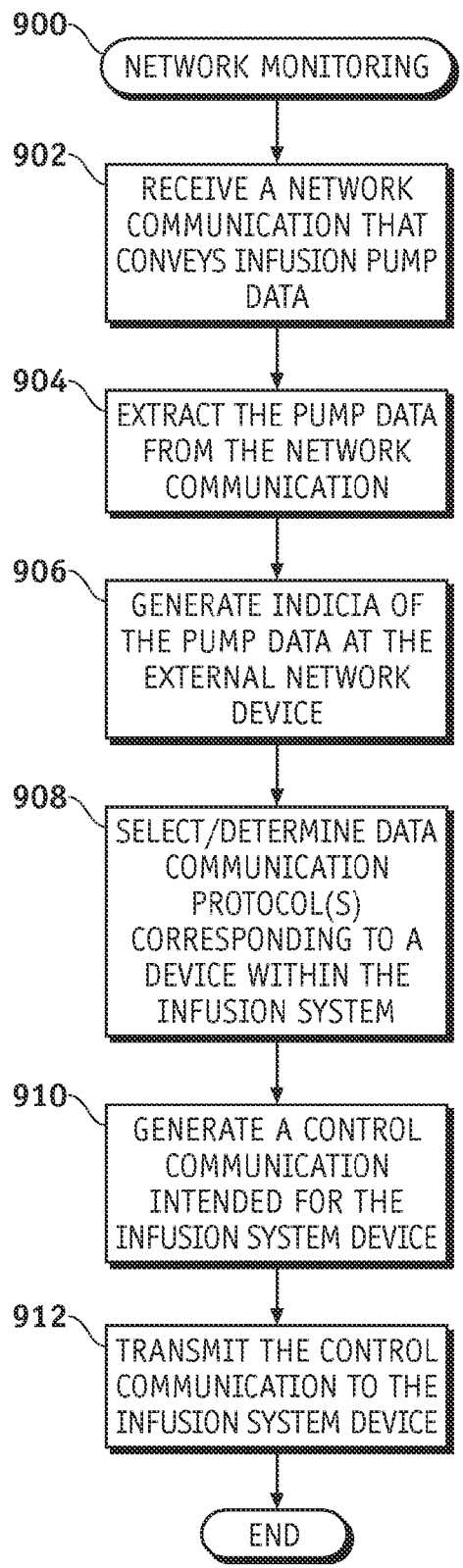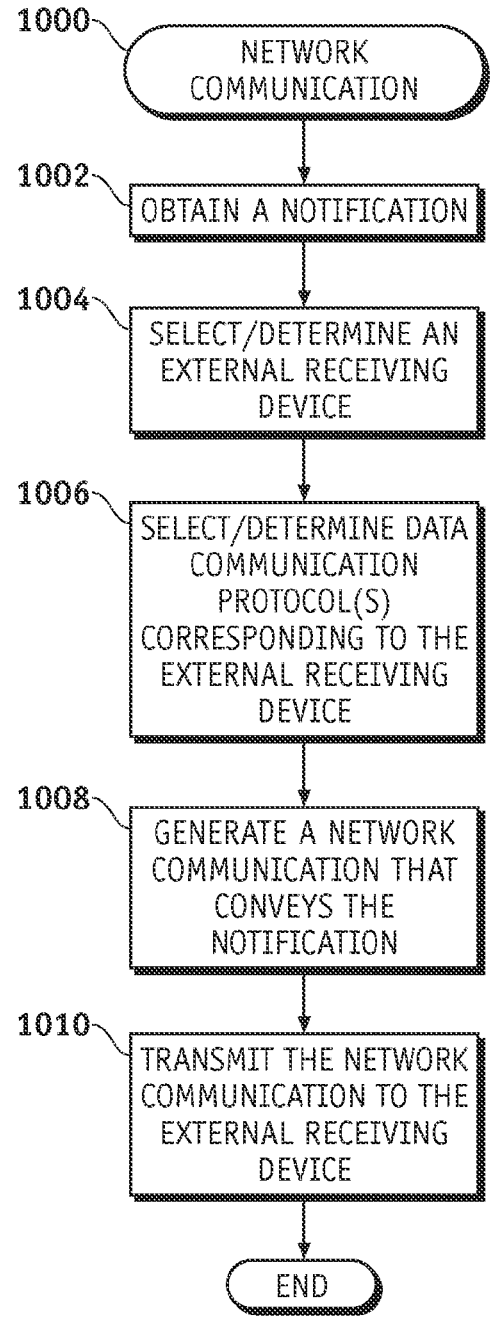
FIG. 9
FIG. 10

REMOTE MONITORING FOR NETWORKED FLUID INFUSION SYSTEMS

CROSS-REFERENCE TO RELATED APPLICATION(S)

This application is a divisional of U.S. patent application Ser. No. 11/414,160, filed Apr. 28, 2006.

TECHNICAL FIELD

Embodiments of the present invention relate generally to infusion systems that deliver fluids into a patient's body. More particularly, embodiments of the present invention relate to systems and techniques related to networked control, management, and monitoring of patient and status information generated by various devices within an infusion system.

BACKGROUND

Diabetics are usually required to modify and monitor their daily lifestyle to keep their body in balance, in particular, their blood glucose ("BG") levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of insulin pump systems that are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. A continuous glucose monitoring system can monitor the patient's BG level in real time.

Insulin pumps and continuous glucose monitoring devices may also be configured to communicate with remote control devices, monitoring or display devices, BG meters, and other devices associated with such an infusion system. Individual devices within conventional infusion systems may be configured to support a limited amount of wired or wireless data communication to support the operation of the infusion system. For example, a continuous glucose monitoring sensor may include a wireless transmitter that communicates with a BG monitor device within the infusion system. As another example, the infusion system may include a handheld remote control that communicates with the infusion pump device using wireless techniques. Conventional infusion systems, however, operate in a somewhat isolated and local manner in that the routing of control signals, monitoring signals, patient status information, physiologic data, alerts, activation instructions, programming signals, and other data communication generally occurs within the limited short range and local operating environment of the infusion system itself.

BRIEF SUMMARY

An embodiment of a medical device system as described here is suitably configured to communicate with one or more external network devices, such as networked computers, cellular telephones, personal digital assistants, hospital monitoring equipment, pager devices, or the like. Network communications from local devices within the medical device system may convey device status information, physiologic patient data, alerts, and/or alarms to the external devices. Such network communications may include notifications to third parties (parents, caregivers, medical equipment manufacturers) transmitted via email, pager messages, telephone calls, or any suitable data communication format. Moreover, network communications from external devices outside the local system environment may convey device programming instructions, device actuation instructions, calibration parameters, alert/alarm enable or disable signals, and/or other control parameters to the local system devices.

The above and other aspects of the invention may be carried out in one embodiment by a monitor device for a medical device system. The monitor device comprises: a first communication module configured to receive a local communication from a transmitting device within the medical device system; a processing architecture coupled to the first communication module, the processing architecture being configured to interpret information conveyed in the local communication; a second communication module coupled to the processing architecture, the second communication module being configured to generate a network communication in response to the information; and a network interface coupled to the second communication module, the network interface enabling transmission of the network communication from the monitor device to a receiving device external to the medical device system.

The above and other aspects of the invention may also be carried out in one embodiment by a handheld monitor/controller device for a medical device system. The monitor device comprises: a first communication module configured to receive a local communication from a transmitting device within the medical device system; a processing architecture coupled to the first communication module, the processing architecture being configured to interpret information conveyed in the local communication; a second communication module coupled to the processing architecture, the second communication module being configured to generate a network communication in response to the information; and a wireless network interface coupled to the second communication module, the wireless network interface enabling wireless transmission of the network communication from the monitor device to a receiving device external to the medical device system.

The above and other aspects of the invention may also be carried out in one embodiment by a method for remote monitoring of an infusion system having an infusion pump that controls the infusion of fluid into the body of a user. The method comprises: receiving, at a network device that is external to the infusion system, a network communication generated by a transmitting device within the infusion system, the network communication conveying pump data associated with the infusion pump; extracting the pump data from the network communication; and generating, at the network device, indicia of the pump data.

The above and other aspects of the invention may also be carried out in one embodiment by a method for a medical device system. The method comprises: obtaining, at a transmitting device within the medical device system, a notification related to operation of a local device; generating a network communication in compliance with a network data communication protocol, the network communication conveying the notification; and transmitting, in accordance with the network data communication protocol, the network communication to a receiving device external to the medical device system.

The above and other aspects of the invention may also be carried out in one embodiment by a network-based medical device system. The system comprises: a monitor device for a medical device system, the monitor device comprising a communication module and a network interface coupled to the communication module, the communication module being configured to generate a network communication; and a network device external to the medical device system, the network device and the network interface being configured to enable transmission of the network communication from the monitor device to the network device via a network communication link.

The above and other aspects of the invention may also be carried out in one embodiment by a communication method for a wireless telemetry router device. The method comprises: receiving, at the wireless telemetry router device, a plurality of wireless communication signals, each of the wireless communication signals conveying sensor data generated by a respective physiological characteristic sensor; generating a network communication in compliance with a network data communication protocol, the network communication conveying at least some of the sensor data; and transmitting, in accordance with the network data communication protocol, the network communication to a network device.

The above and other aspects of the invention may also be carried out in one form by a data communication device comprising: a wireless communication module configured to support wireless data communication with a wireless medical device operating within a local system; a memory element coupled to the wireless communication module and configured to store data conveyed in wireless signals received from the wireless medical device; and a network interface coupled to the wireless communication module and configured to support transmission of network communications between the data communication device and a network device.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

FIG. 9 is a flow chart that depicts an example network-based infusion system monitoring process;

FIG. 10 is a flow chart that depicts an example network-based infusion system communication process;

DETAILED DESCRIPTION

Figure 1:
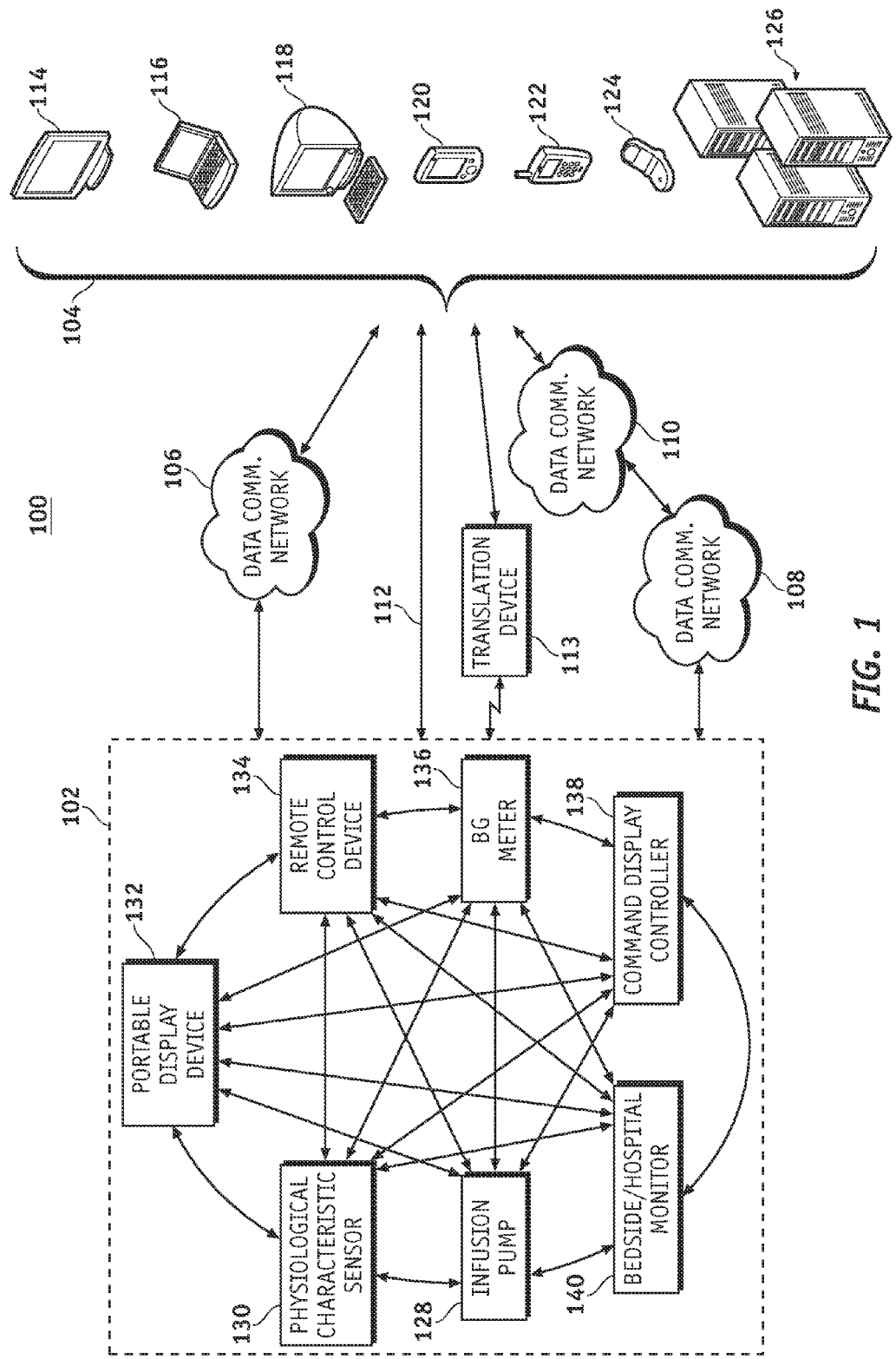
FIG. 1 is a schematic representation of a network-based infusion system configured in accordance with an example embodiment of the invention.

The following detailed description is merely illustrative in nature and is not intended to limit the embodiments of the invention or the application and uses of the embodiments of the invention. Furthermore, there is no intention to be bound by any expressed or implied theory presented in the preceding technical field, background, brief summary or the following detailed description.

Embodiments of the invention may be described here in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present invention may be practiced in conjunction with any number of data transmission protocols and that the system described here is merely one exemplary application for embodiments of the invention.

For the sake of brevity, conventional techniques related to infusion system operation, insulin pump and/or infusion set operation, blood glucose sensing and monitoring, signal processing, data transmission, signaling, network control, and other functional aspects of the systems (and the individual operating components of the systems) may not be described in detail here. Examples of infusion sets that may be used as a delivery device are described in, but not limited to, U.S. Pat. Nos. 4,723,947; 4,755,173; 5,176,662; 5,584,813; 6,056,718; 6,461,329; 6,475,195; 6,520,938; 6,585,695; 6,591,876; and 6,607,509, which are herein incorporated by reference. Examples of infusion pumps and/or communication options may be of the type described in, but not limited to, U.S. Pat. Nos. 4,562,751; 4,685,903; 5,080,653; 5,505,709; 5,097,122;

6,554,798; 6,558,320; 6,558,351; 6,641,533; 6,659,980; 6,752,787; 6,817,990; and 6,932,584, which are herein incorporated by reference. Examples of glucose sensing and/or monitoring devices maybe be of the type described in, but not limited to, U.S. Pat. Nos. 6,484,045; 6,809,653; 6,892,085; and 6,895,263, which are herein incorporated by reference. Furthermore, the connecting lines shown in the various figures contained here are intended to represent example functional relationships and/or physical couplings between the various elements. It should be noted that many alternative or additional functional relationships or physical connections may be present in an embodiment.

The following description may refer to elements or features being "connected" or "coupled" together. As used here, unless expressly stated otherwise, "connected" means that one element/feature is directly joined to (or directly communicates with) another element/feature, and not necessarily mechanically. Likewise, unless expressly stated otherwise, "coupled" means that one element/feature is directly or indirectly joined to (or directly or indirectly communicates with) another element/feature, and not necessarily mechanically. Thus, although each of the schematic block diagrams depicts one example arrangement of elements, additional intervening elements, devices, features, or components may be present in an embodiment (assuming that the functionality of the device or system is not adversely affected).

FIG. 1 is a schematic representation of a network-based medical device system 100 configured in accordance with an example embodiment of the invention. In this example, system 100 is an insulin infusion system that controls the infusion of insulin into the body of a user. Aspects of the invention, however, may also be utilized in the context of other medical device systems. Briefly, system 100 includes a local infusion system 102 having one or more local devices that communicate (unidirectional or bidirectional) with one or more network devices 104. As used here, network devices 104 are "external" to local infusion system 102 because they need not utilize the local data communication protocols and techniques employed within local infusion system 102, and because they need not be in close physical proximity to the local devices within local infusion system 102. The manner in which a given local device within local infusion system 102 communicates with a given network device 104 may vary depending upon the particular configuration of system 100, the characteristics of that local device, and the characteristics of that network device 104. For example, network communications may be routed using one data communication network 106, using a plurality of data communication networks 108/110, using a direct wireless or wired connection 112, or the like. In one example embodiment, data from wireless devices within local infusion system 102 (and/or data from wireless devices associated with different local infusion systems) may be collected by a wireless telemetry router device that serves as an interface to one or more network devices 104. One example wireless telemetry router device is described in more detail below in connection with FIG. 21.

Data communicated within local infusion system 102 and/or between devices within local infusion system 102 and network devices 104 may include or represent, without limitation: physiologic patient data, device status information, time and date information, alarm/alert status, and other information related to the operation, status, or condition of the patient, related to any of the devices within local infusion system 102, or related to local infusion system 102 itself. For example, such data may include or represent bolus information, basal information, or sensor information. Such data may also include or represent information entered by the patient, a caregiver, or another person having access to a local device or a network device 104, such as, without limitation: reminders; event markers (for meals, exercise, or the like); alarms; notifications; or the like.

In one embodiment, devices within local infusion system 102 can communicate with network devices 104 via a suitably configured translation device, system, or application 113. For example, such a translation device 113 may be configured to communicate with devices within local infusion system 102 using a suitable RF data communication protocol (which may be published or proprietary), while coupling to one or more network devices 104 via a standardized data communication interface such as USB, IEEE 1394, or the like. The translation device 113 may also be provisioned with flash memory capability such that patients or caregivers can save data received from a device in a portable storage device and physically transport the storage device to any compatible computing device, e.g., a personal computer at a doctor's office. One example translation device is described in more detail below in connection with FIGS. 18-20.

As used here, a "data communication network" represents any number of physical, virtual, or logical components, including hardware, software, firmware, and/or processing logic configured to support data communication between an originating component and a destination component, where data communication is carried out in accordance with one or more designated communication protocols over one or more designated communication media. Communication hardware utilized by a data communication network may include a mechanically detachable unit such as an SDIO, a USB ready wireless module, or the like. For example, data communication network 106 may include, without limitation: a computer network such as a local area network or a wide area network; a pager network; a cellular telecommunication network; a cordless telephone system; an 802.11 network (WiFi); an 802.16 network (WiMAX); the Internet; IEEE P1901 BPL (Broadband over Power Lines); a hospital data communication network (WMTS or other); a home network, such as a home control network, a home security system, or a home alarm system; the public switched telephone network; a satellite communication network; or the like. In embodiments, network communications between local infusion system 102 and network devices 104 may be routed by two or more different types of data communication networks using known or proprietary network interfacing techniques.

The flexible nature of network-based infusion system 100 is illustrated in FIG. 1, which depicts local infusion system 102 in communication with a variety of external and remote network devices 104. In an embodiment, local devices within local infusion system 102 may be suitably configured to support the transmission of network communications to: a stationary monitor device 114, such as a bedside monitor or a piece of hospital monitoring equipment; a portable computer 116, such as a laptop PC, a palmtop PC, or a tablet PC; a stationary computer 118, such as a desktop PC; a personal digital assistant 120, which may also be a portable email device; a smart phone 122, which may also be a portable email device; a wireless phone 124, such as a cellular phone or a cordless phone; one or more additional computing devices or databases 126; or the like. As described in more detail below, these local devices need not communicate only via a local network interface and such devices may communicate using other means. The above list of possible network devices 104 is not exhaustive, and an implementation of system 100 can be designed to accommodate network communication with other network systems, equipment, computing devices, components, and elements that are external to local infusion system 102.

In one embodiment, local infusion system 102 is realized as an insulin infusion system that is locally controlled and monitored by the patient. In this example, local infusion system 102 includes at least an infusion pump 128. Local infusion system 102 may also include any of the following components, without limitation: a physiological characteristic sensor 130, such as a continuous glucose sensor (which may include a wireless transmitter); a portable display device 132; a remote control device 134; a BG meter 136 or other physiological characteristic meter; a command display controller 138 for infusion pump 128; and a monitor device 140, which may be realized as a bedside monitor or a hospital monitor. Each of these local devices is described in more detail below.

As depicted in FIG. 1, these local devices may be configured to transmit and receive local communications within local infusion system 102, where such local communications are transmitted and received in accordance with one or more specified local data communication protocols. For example, local communications may be exchanged between local devices using one or more wireless data communication protocols (which may leverage RF, infrared, magnetic induction, or other wireless techniques) and/or using one or more wired data communication protocols. Local infusion system 102 may be flexibly configured such that any given local device can communicate with any other local device, and a communication link or path between two local devices may be unidirectional or bidirectional. FIG. 1 depicts an example embodiment where each communication link or path is bidirectional (represented by double headed arrows).

Infusion pump 128 is configured to deliver fluid, such as insulin, into the body of a user via, for example, an infusion set. In accordance with one example embodiment, infusion pump 128 serves as a central hub, and most of the processing logic and intelligence for local infusion system resides at infusion pump 128. In some embodiments, the local medical device system need not include infusion pump 128, for example, monitoring systems utilized in conjunction with traditional insulin injection therapy. Moreover, infusion pump 128 need not include a display. In an embodiment that lacks a display, portable display device 132, remote control device 134, command display controller 138, or any other device within local infusion system 102 may serve as a remote display for infusion pump 128. Other options for a remote display include, but are not limited to, any of the network devices 104 described above, e.g., wireless phone 124, monitor device 114, portable computer 116, or personal digital assistant 120.

In practice, operation of infusion pump 128 may be remotely controlled by command display controller 138 (which may be realized as a handheld monitor/controller for infusion pump 128), by remote control device 134, and/or by or monitor 140. In one example embodiment, BG meter 136 may include the functionality of a controller device such that both components share a single housing. One such BG meter is described in U.S. patent application Ser. No. 11/204,667, titled "Controller Device for an Infusion Pump," the content of which is incorporated by reference herein. Control of infusion pump 128 may also be possible via a suitably configured user interface located at infusion pump 128 itself.

Local infusion system 102 may also include physiologic characteristic sensor 130, which is suitably configured to measure a physiologic characteristic of the patient. In addition, sensor 130 may include processing and control logic that enables it to control the operation of infusion pump 128. Such control may be responsive to measurements obtained by sensor 130. In the example system described here, sensor 130 is a continuous BG sensor that measures the BG level of the patient in real time. Sensor 130 may include a wireless transmitter that facilitates transmission of physiologic data of the user to other devices within local infusion system 102. Alternatively, sensor 130 may be directly wired to a monitor/user interface. Sensor 130 may also be linked to monitor 140 so that monitoring and programming of medication delivery may be performed remotely. Alternatively sensor 130 may communicate directly with devices in the external network space, e.g., via Bluetooth, ZigBee or the like.

Local devices can process the received sensor data in an appropriate manner. For example, portable display device 132, remote control device 134, BG meter 136, command display controller 138, monitor 140, or infusion pump 128 may display the current BG level derived from the received sensor data and/or generate an alert or otherwise indicate low or high BG levels. As another example, BG meter 136 or infusion pump 128 may process the received sensor data for purposes of calibration. As yet another example, infusion pump 128 may be configured to activate its infusion mechanism in response to the received sensor data. Moreover, sensor data could be processed in one or more of the local devices and/or in one or more of network devices 104. In this regard, system 100 may utilize distributed processing techniques for the handling of sensor data.

Any of the devices within local infusion system 102 may include a display and related processing logic that facilitates the display of physiologic patient data, device status information, time and date information, alarm/alert status, and other information related to the operation, status, or condition of the patient, related to any of the devices within local infusion system 102, or related to local infusion system 102 itself Portable display device 132 may be realized as a small device having limited functionality. In this regard, portable display device 132 may be incorporated into a key fob, a carabiner, a pendant, an insulin pen, a credit card display, or the like. Other local devices may have expanded display capabilities related to the specific functionality of such devices. For example, BG meter 136 may include display features that are specific to its metering functionality.

BG meter 136 is generally configured to measure the BG level of a user by analyzing a blood sample. For example, BG meter 136 may include a receptacle for receiving a blood sample test strip. In this regard, the user inserts a test strip into the BG meter 136, which analyzes the sample and displays a BG level corresponding to the test strip sample. BG meter 136 may be configured to generate a local communication, which conveys the measured BG level, for transmission to other local devices within local infusion system 102. Depending upon the specific application, BG meter 136 may also include the functionality of a monitoring device for infusion pump 128 and/or the functionality of a controller device for infusion pump 128.

Command display controller 138 is preferably realized as a handheld monitor/controller device that, although physically separate from infusion pump 128, enables the user to monitor and control the operation of infusion pump 128. This allows the user to operate infusion pump 128 without physically handling the device. As described in more detail below, command display controller 138 includes a communication module for transmitting local communications or commands to infusion pump 128. In further embodiments, command display controller 138 may receive local communications sent from infusion pump 128 or other components within local infusion system 102. In example embodiments, command display controller 138 also includes a network communication module for handling network communications to and from network devices that are external to local infusion system 102. Further, command display controller 138 may include one or more user input elements on its housing, such as keys, buttons, or the like, which accommodate user inputs. In embodiments, command display controller 138 includes a display on its housing, which may be configured to concurrently reproduce at least a portion of the information displayed on infusion pump 128.

Monitor 140, which may be realized as a bedside monitor for personal use or as a hospital monitor for caregiver use, enables remote monitoring of infusion pump 128 (and possibly other devices within local infusion system 102). Monitor 140 and other monitors described herein may be utilized in applications that do not utilize infusion pump 128; for example, applications that monitor patient data (such as glucose levels). In addition, monitor 140 may be suitably configured to enable remote programming and control of infusion pump 128 and/or other devices within local infusion system 102. In this regard, a "monitor" as used herein can generally refer to a monitor-only device or a monitor-controller device. In practice, monitor 140 is a relatively large device in comparison to portable or handheld devices of infusion system 102. In contrast to remote control device 134, portable display device 132, and command display controller 138, monitor 140 is intended to be somewhat stationary and not carried by the user. For example, a bedside monitor may be located on a nightstand beside the patient's bed, while a hospital monitor may be located on a medical equipment cart or stand in the patient's room. In contrast to the smaller portable devices of local infusion system 102, monitor 140 preferably includes a large and easy to read display element, which may be configured to concurrently reproduce at least a portion of the information displayed on infusion pump 128.

As described above in connection with command display controller 138, monitor 140 may also be configured to allow the user to remotely operate infusion pump 128. Monitor 140 may include a communication module for receiving and/or transmitting local communications within local infusion system 102. Moreover, monitor 140 may include a network communication module for handling network communications to and from network devices that are external to local infusion system 102. Further, monitor 140 may include one or more user input elements on its housing, such as keys, buttons, or the like, which accommodate user inputs.

As shown in FIG. 1, local infusion system 102 is capable of establishing many potential communication paths between the local devices. In embodiments, a controller device (e.g., remote control device 134, command display controller 138, or monitor 140) may serve as a translator between infusion pump 128 and the other components of local infusion system 102, such as BG meter 136. For example, the controller device may have the ability to determine how best to translate data received from infusion pump 128 for compatibility with the display requirements of a destination device within local infusion system 102. As depicted in FIG. 1, infusion pump 128 may communicate directly with BG meter 136. In some embodiments, local infusion system 102 may include multiple controllers that can communicate with infusion pump 128. In other embodiments, only one controller device can communicate with infusion pump 128 at any given moment. The controller device functionality may also be integrated into infusion pump 128 in some embodiments. In yet another embodiment, BG meter 136 may be integrated into the controller device such that both features share a single device housing.

Figure 2:
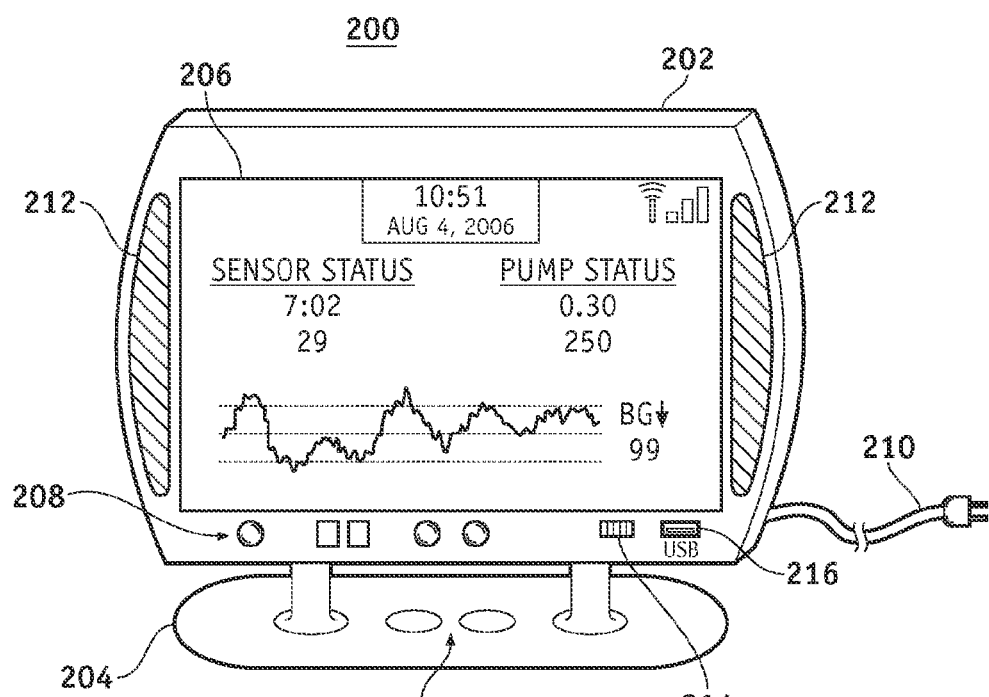
FIG. 2 is a front view of a bedside infusion system monitor configured in accordance with an example embodiment of the invention.

FIG. 2 is a front view of an example bedside monitor 200 configured in accordance with an example embodiment of the invention. Referring to FIG. 1, bedside monitor 200 may be deployed in local infusion system 102 (as monitor 140) and/or as a network device 104 (e.g., as monitor 114). Bedside monitor 200 may, but need not, be utilized to monitor the activity of an insulin infusion pump. Bedside monitor 200 generally includes a housing 202, a stand 204 that supports housing 202, a display element 206, and user interface features 208. Embodiments of bedside monitor 200 may include an AC power plug 210, one or more speakers 212, one or more local device interfaces 214, and one or more network interfaces 216.

As mentioned above, bedside monitor 200 is intended to be used as a somewhat stationary fixture placed in a suitable location, such as on the patient's nightstand. In other words, bedside monitor 200 is not designed to be a portable or handheld component. Therefore, housing 202 may be sized to accommodate a relatively large display element 206, which may utilize any known display technology (e.g., a cathode ray tube, an LCD panel, or a plasma panel). The size of display element 206 may vary to suit the needs of the particular application; typical sizes can range from 10 diagonal inches to 20 diagonal inches. Housing 202 may also be configured to accommodate integral speakers 212, which can be activated to generate alarm or alert notifications. Housing 202 may also be designed to accommodate user interface features 208 as shown in FIG. 2. Stand 204 is suitably configured to support housing 202 and to provide a stable mounting location for bedside monitor 200. In the example embodiment shown in FIG. 2, stand 204 is also configured to accommodate one or more user interface features 208. User interface features 208 may include a keypad, keys, buttons, switches, knobs, a touchpad, a joystick, a pointing device, a virtual writing tablet, or any device, component, or function that enables the user to select options, input information, or otherwise control the operation of bedside monitor 200.

Bedside monitor 200 may include processing logic, a display driver, and memory (not shown in FIG. 2) that is suitably configured to display information on display element 206. In embodiments, bedside monitor 200 functions to display information requested by the user, to display information related to an instructed act that was undertaken by the infusion pump, or to display status data for the infusion pump, such as, for example, BG levels, BG trends or graphs, or fluid delivery information. Bedside monitor 200 may be configured to display information conveyed in local communications received from an infusion pump or from any device within the local infusion system. At any moment, display element 206 may show substantially the same information as shown on the infusion pump; the two displays may mimic one another so that the user may choose to conveniently view the selected information from bedside monitor 200 rather than from the infusion pump, which is usually attached to the patient's body through an infusion set. Display element 206 may also include a backlight to facilitate viewing. The backlight may be a user programmable multi-color backlight that additionally performs the function of a visual indicator by flashing colors appropriate to the level of an alert or alarm. The backlight may also have variable intensity (automatic or manual) to accommodate user preferences and/or to indicate different alert or alarm status.

As described in more detail below, bedside monitor 200 may include one or more communication modules (not shown in FIG. 2) that facilitate data communication between bedside monitor 200 and other local devices within the local infusion system and/or data communication between bedside monitor 200 and network devices that are external to the local infusion system. For example, a local communication module may cooperate with a local device interface to receive local communications from local devices and/or to transmit local communications to local devices. The local communication module and local device interface may be configured to support wireless and/or wired data communication protocols. In an embodiment, local device interface 214 may represent a physical interface (such as a plug, a jack, a connector, a USB port, etc.) that facilitates connection to a data communication cable or any suitably configured physical component that establishes a communication link to a local device. As another example, a network communication module may cooperate with a network interface to receive network communications from network devices and/or to transmit network communications to network devices. The network communication module and network interface may be configured to support wireless and/or wired data communication protocols. In an embodiment, network interface 216 may represent a physical interface (such as a plug, a jack, a connector, a USB port, etc.) that accommodates a data communication cable or any suitably configured physical component that establishes a communication link to a network device. Bedside monitor 200 may also utilize one or more wireless local device interfaces and one or more wireless network interfaces, however, such wireless interfaces may not be visible from points outside housing 202.

Figure 3:
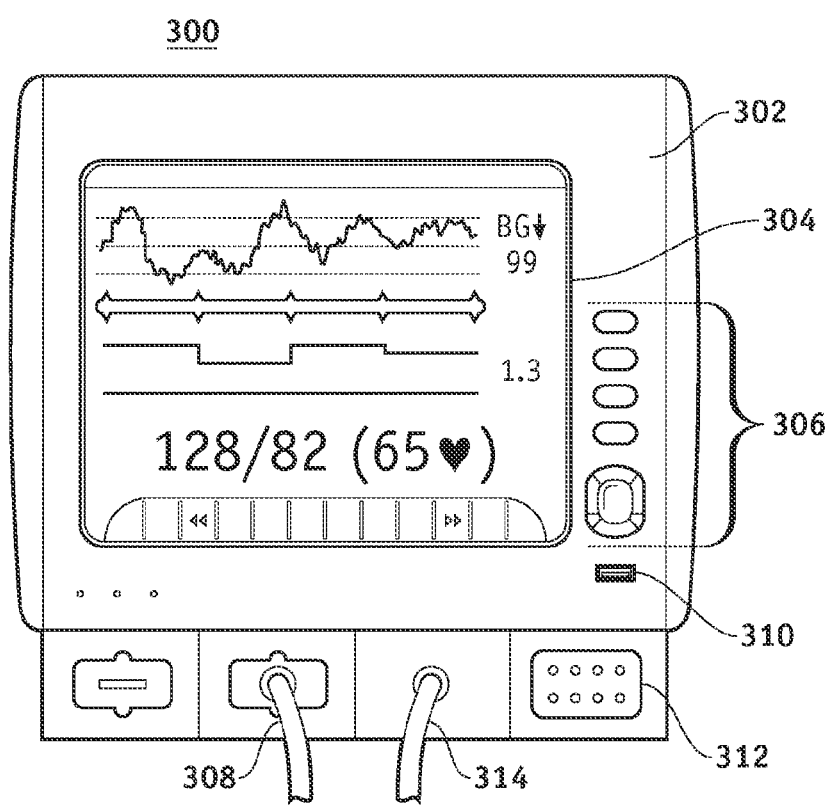
FIG. 3 is a front view of a hospital infusion system monitor configured in accordance with an example embodiment of the invention.

FIG. 3 is a front view of an example hospital monitor 300 configured in accordance with an example embodiment of the invention. Hospital monitor 300 is similar to bedside monitor 200, and both monitors include some shared features and functionality. For the sake of brevity, such common features and functions will not be redundantly described here. Hospital monitor 300 is generally configured to display and/or process information in an appropriate manner. Such information may be, for example, alarms, alerts, or any of the information or data types described above with respect to FIG. 1, regardless of the location or device that originally generated or processed such information/data. Generally, referring to FIG. 1, hospital monitor 300 may be deployed in local infusion system 102 (as monitor 140) and/or as a network device 104 (e.g., as monitor 114). Hospital monitor 300 generally includes a housing 302, a display element 304, user interface features 306, an AC power plug 308, one or more speakers (hidden from view in FIG. 3), one or more local device interfaces 310, and one or more network interfaces 312. In this example embodiment, hospital monitor 300 also includes an integrated infusion pump that delivers fluid to the patient via a delivery tube 314.

Hospital monitor 300 is intended to be used as a somewhat stationary fixture placed in a suitable location, such as on a cart or an equipment rack in the patient's room. In other words, hospital monitor 300 is not designed to be a portable or handheld component. Hospital monitor 300 is suitably configured to operate substantially as described above with respect to bedside monitor 200. In contrast to bedside monitor 200, however, hospital monitor 300 may include an infusion pump and control features related to the operation of the infusion pump. Moreover, hospital monitor 300 may employ a network communication module and a network interface that cooperate to receive network communications from hospital network devices and/or to transmit network communications to hospital network devices. As used here, a "hospital network" refers to any number of physical or logical components, including hardware, software, firmware, and/or processing logic configured to support data communication between an originating component and a destination component, where data communication is carried out in accordance with one or more communication protocols that are reserved for, or utilized in, hospital environments.

Figure 4A:
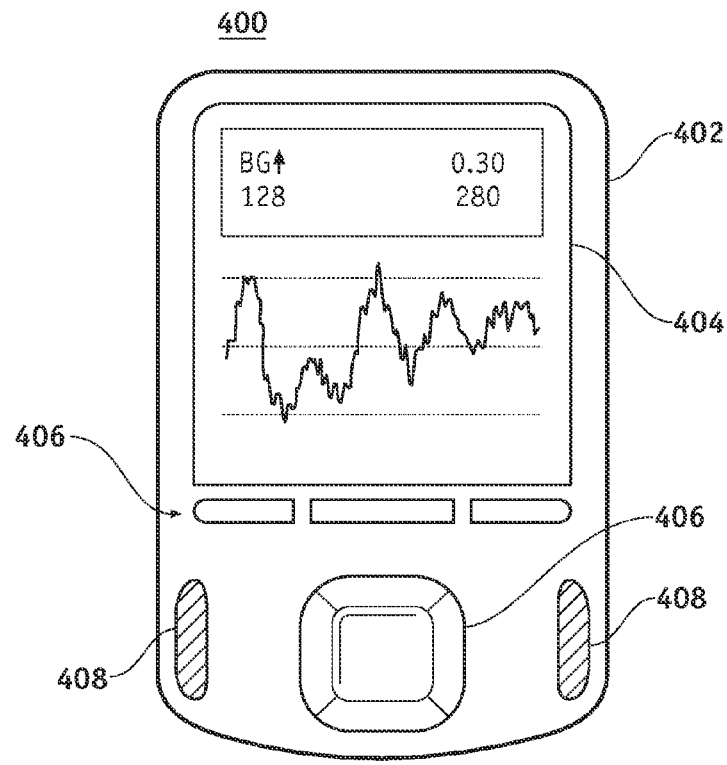
FIG. 4A is a front view of a handheld infusion system monitor/controller configured in accordance with example embodiment of the invention.

FIG. 4A is a front view of a handheld monitor/controller 400 configured in accordance with an example embodiment of the invention. Handheld monitor/controller 400 is similar to bedside monitor 200, and both monitors include some shared features and functionality. For the sake of brevity, such common features and functions will not be redundantly described here. Referring to FIG. 1, handheld monitor/controller 400 may be deployed in local infusion system 102 (as command display controller 138 or remote control device 134) and/or as a network device 104 (e.g., as personal digital assistant 120). Handheld monitor/controller 400 generally includes a housing 402, a display element 404, user interface features 406, one or more speakers 408, one or more local device interfaces (not shown), and one or more network interfaces (not shown).

Handheld monitor/controller 400 is intended to be used as a portable and mobile device that can be carried by the user. In particular embodiments, handheld monitor/controller 400 supports wireless communication with the patient's infusion pump, and the telemetry range of handheld monitor/controller 400 is localized. Handheld monitor/controller 400 is suitably configured to operate substantially as described above in connection with bedside monitor 200. Although the example embodiment utilizes a wireless local device interface and a wireless network interface, handheld monitor/controller 400 may also include wired interfaces to accommodate direct physical connections to other devices within the local infusion system and/or to network devices external to the local infusion system.

The power of handheld monitor/controller 400 (and of the other portable devices discussed here) may be provided by a battery. The battery may be a single use or a rechargeable battery. Where the battery is rechargeable, there may be a connector or other interface on handheld monitor/controller 400 for attaching the device to an electrical outlet, docking station, portable recharger, or so forth to recharge the battery while the battery remains in housing 402. It is also possible that a rechargeable battery may be removable from housing 402 for external recharging. In practice, however, the rechargeable battery may be sealed into housing 402 to create a more water resistant or waterproof component. In further embodiments, handheld monitor/controller 400 may be adapted to accommodate more than one type of battery. For example, handheld monitor/controller 400 may be configured to accommodate a rechargeable battery and (for backup or emergency purposes) a readily available battery type, such as a AA battery, a AAA battery, or a coin cell battery.

Figure 4B:
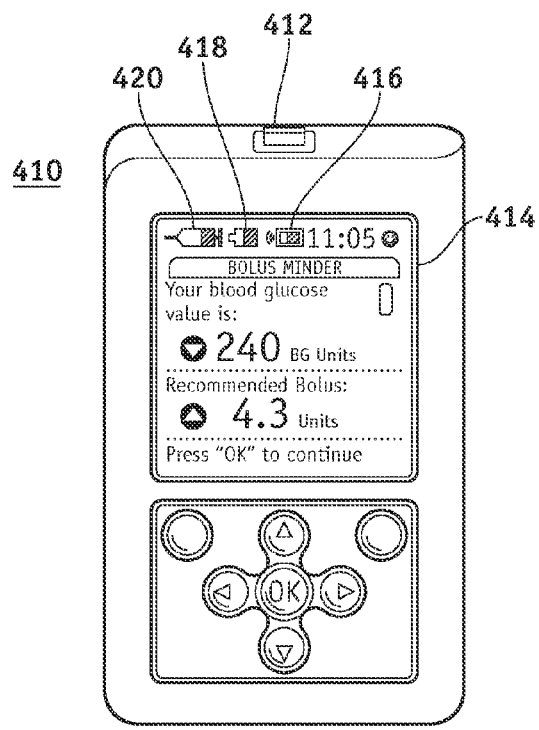
FIG. 4B is a front view of a handheld infusion system monitor/controller configured in accordance with another example embodiment of the invention.

FIG. 4B is a front view of a handheld monitor/controller 410 configured in accordance with another example embodiment of the invention. Handheld monitor/controller 410 is similar to handheld monitor/controller 400, and both devices include some shared features and functionality. For the sake of brevity, such common features and functions will not be redundantly described here.

Handheld monitor/controller 410 preferably includes wireless data communication functionality that enables it to handle wireless local communications and/or wireless network communications. In addition, handheld monitor/controller 410 may include a wired or cabled network interface 412, which may be realized as a cable connector, jack, plug, or receptacle. FIG. 4B depicts example content displayed on a display element 414 of handheld monitor/controller 410. This content represents one particular "screen shot" for handheld monitor/controller 410; in practice any number of different display screens can be generated to suit the intended functionality and features of the device. The example screen shot of FIG. 4B includes a clock display, an RF quality indicator 416, a battery indicator 418, a fluid level indicator 420 that represents the amount of fluid remaining in the infusion pump, a current BG value for the patient (240 in this example), and a recommended bolus (4.3 units in this example). Handheld monitor/controller 410 may also display one or more prompts that provide guidance or instruction to the user. In this example, display element 414 includes the prompt: "Press 'OK' to Continue". The user can press "OK" to display other options, such as an activation request that controls the infusion pump to administer the recommended bolus.

Figure 5:
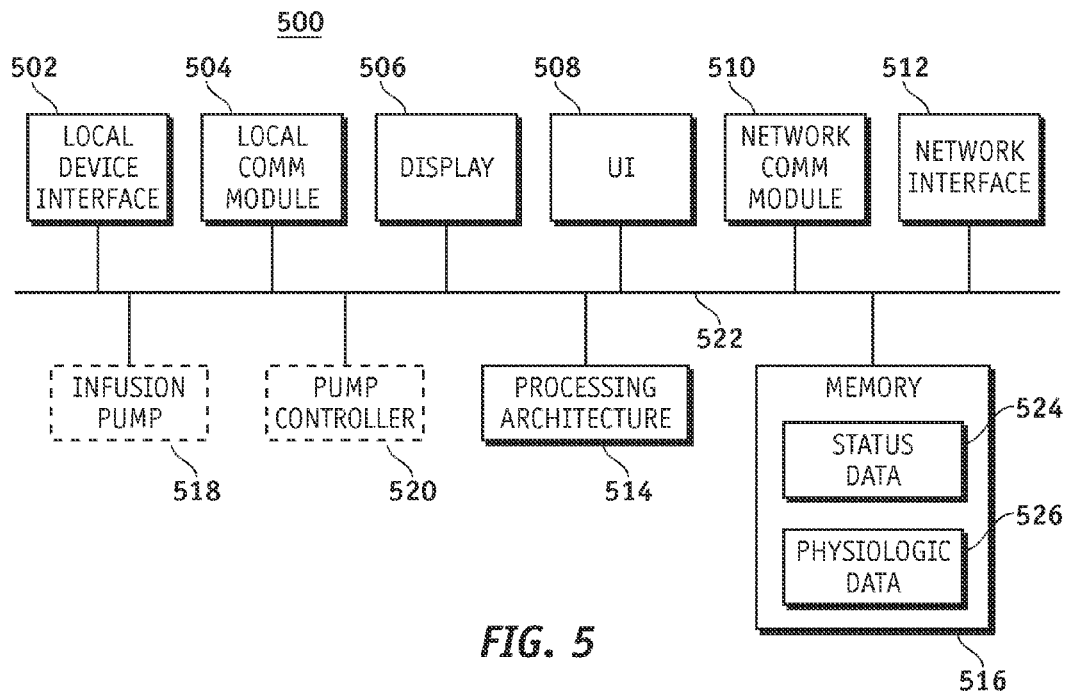
FIG. 5 is a schematic representation of an infusion system monitor configured in accordance with an example embodiment of the invention.

FIG. 5 is a schematic representation of a medical device system monitor 500 configured in accordance with an example embodiment of the invention. Monitor 500 represents a generalized embodiment that may be realized as a bedside monitor, a hospital monitor, or a handheld monitor/controller, depending upon its specific configuration. In this example, monitor 500 generally includes a local device interface 502, a local communication module 504, a display element 506, one or more user interface features 508, a network communication module 510, a network interface 512, a processing architecture 514, and a suitable amount of memory 516. If monitor 500 is implemented as a hospital monitor, then it may also include an infusion pump 518 and a pump controller 520 that controls the operation of infusion pump 518 (these elements are depicted in dashed lines to indicate their optional nature). The elements of monitor 500 may be coupled together via a bus 522 or any suitable interconnection architecture.

Those of skill in the art will understand that the various illustrative blocks, modules, circuits, and processing logic described in connection with monitor 500 (and other devices, elements, and components disclosed here) may be implemented in hardware, computer software, firmware, or any combination of these. To clearly illustrate this interchangeability and compatibility of hardware, firmware, and software, various illustrative components, blocks, modules, circuits, and processing steps may be described generally in terms of their functionality. Whether such functionality is implemented as hardware, firmware, or software depends upon the particular application and design constraints imposed on the embodiment. Those familiar with the concepts described here may implement such functionality in a suitable manner for each particular application, but such implementation decisions should not be interpreted as causing a departure from the scope of the present invention.

Referring again to FIG. 5, display element 506 and user interface features 508 were described above in connection with bedside monitor 200, hospital monitor 300, and handheld monitor/controller 400. Briefly, display element 506 is suitably configured to enable monitor 500 to display physiologic patient data, local device status information, clock information, alarms, alerts, and any information/data received or processed by monitor 500. For example, display element 506 may be controlled to indicate an alert or alarm status when monitor 500 receives an incoming communication (from a local device within the infusion system or from a network device external to the infusion system) that conveys an alert signal or an alarm signal. User interface features 508 enable the user to control the operation of monitor 500. In one example embodiment, user interface features 508 enable the user to control the operation of one or more additional devices within the local infusion system, for example, an infusion pump. Moreover, monitor 500 may be configured such that user interface features 508 can be manipulated to control the operation of one or more network devices that are external to the local infusion system.

Processing architecture 514 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor may be realized as a microprocessor, a controller, a microcontroller, or a state machine. Moreover, a processor may be implemented as a combination of computing devices, e.g., a combination of a digital signal processor and a microprocessor, a plurality of microprocessors, one or more microprocessors in conjunction with a digital signal processor core, or any other such configuration.

In practice, processing architecture 514 may be suitably configured to interpret and process incoming information, data, and content that is conveyed in local communications received from a transmitting device within the local infusion system. Referring to FIG. 1, the transmitting device may be any of the devices within local infusion system 102, including another monitor device. Such incoming information may include, without limitation: physiologic data of the user, such as a BG level (a calibrated reading or a raw measured value); status information of the transmitting local device (e.g., a battery life indication, a power on/off status, a transmit signal power level, diagnostic information indicating results of self tests); an alert signal related to operation of the transmitting local device (e.g., a low battery alert, an out of range alert, a calibration reminder); a basal rate of fluid delivered to the user by an infusion pump; bolus information for a bolus of fluid delivered to the user by an infusion pump; advisory information for the patient (e.g., a notification to place an order for supplies, a reminder to schedule a doctor's appointment, a reminder to schedule or automatically execute a data download for analysis by a caregiver, a notification to perform routine diagnostics, either manually or remotely via a network connection); or the like.

Processing architecture 514 may also be configured to interpret and process incoming information, data, and content that is conveyed in network communications generated by an originating device that is external to the local infusion system. Referring to FIG. 1, the originating device may be any network device 104, including a networked monitor device. Such incoming network information may include, without limitation: programming data for a local device within the infusion system; an activation instruction for an infusion pump or another local device within the infusion system; a status request for a local device within the infusion system; a request for physiologic data of the user; an alert or alarm enable or disable instruction for a local device within the infusion system (which may be processed by monitor 500 and/or routed by monitor 500 to the appropriate local device); advisory information for the patient (e.g., a notification to place an order for supplies, a reminder to schedule a doctor's appointment, a reminder to schedule or automatically execute a data download for analysis by a caregiver, a notification to perform routine diagnostics, either manually or remotely via a network connection); or the like.

Memory 516 may be realized as RAM memory, flash memory, EPROM memory, EEPROM memory, registers, a hard disk, a removable disk, a CD-ROM, or any other form of storage medium known in the art. In this regard, memory 516 can be coupled to processing architecture 514 such that processing architecture 514 can read information from, and write information to, memory 516. In the alternative, memory 516 may be integral to processing architecture 514. As an example, processing architecture 514 and memory 516 may reside in an ASIC. In this example, memory 516 may be utilized to store device status data 524 and/or physiologic data 526 of the user, where such data is communicated to monitor 500 via local communications, network communications, or directly (for example, if monitor 500 is configured to receive BG data directly from a test strip or via direct user input).

Monitor 500 may be configured to communicate with a remote database or databank that is accessible via a network connection. Referring to FIG. 1, for example, a network device 104 in system 100 may be realized as a network database 126 that provides data to monitor 500. In such an embodiment, monitor 500 can download data from the remote database as necessary, store it in memory 516 if needed, or otherwise process the downloaded data in an appropriate manner.

An embodiment of monitor 500 may employ any number of local communication modules 504 and any number of local device interfaces 502. For simplicity, the example described here employs one local communication module 504 and one local device interface 502. Local communication module 504 and local device interface 502 are suitably configured to support local communications between monitor 500 and devices within the local infusion system (e.g., any of the devices in infusion system 102 shown in FIG. 1). Depending upon the particular implementation, local communication module 504 and local device interface 502 may be configured to support unidirectional communication from monitor 500 to one or more local devices, unidirectional communication from one or more local devices to monitor 500, or bidirectional communication between monitor 500 and one or more local devices. Thus, local device interface 502 may be configured to receive a local communication from a transmitting device within the local infusion system, and/or to transmit a local communication to a receiving device within the local infusion system. Moreover, depending upon the particular implementation, local communication module 504 and local device interface 502 may be configured to support wireless data communication, wired/cabled data communication, or both.

For wireless transmissions of local communications, local communication module 504 and local device interface 502 support one or more wireless data communication protocols that are also supported by the local device(s) communicating with monitor 500. Any number of suitable wireless data communication protocols, techniques, or methodologies may be supported by monitor 500, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. In an embodiment, a wireless local device interface 502 may include or be realized as hardware, software, and/or firmware, such as an RF front end, a suitably configured radio module (which may be a stand alone module or integrated with other or all functions of the device), a wireless transmitter, a wireless receiver, a wireless transceiver, an infrared sensor, an electromagnetic transducer, or the like.

For transmissions of local communications over a cable, a wired connection, or other physical link, local communication module 504 and local device interface 502 support one or more wired/cabled data communication protocols that are also supported by the local device(s) communicating with monitor 500. Any number of suitable data communication protocols, techniques, or methodologies may be supported by monitor 500, including, without limitation: Ethernet; home network communication protocols; USB; IEEE 1394 (Firewire); hospital network communication protocols; and proprietary data communication protocols. In an embodiment, a wired/cabled local device interface 502 may include or be realized as hardware, software, and/or firmware, such as a suitably configured and formatted port, connector, jack, plug, receptacle, socket, adaptor, or the like.

An embodiment of monitor 500 may employ any number of network communication modules 510 and any number of network interfaces 512. For simplicity, the described example employs one network communication module 510 and one network interface 512. Network communication module 510 and network interface 512 are suitably configured to support network communications between monitor 500 and network devices that are external to the local infusion system (e.g., one or more of the network devices 104 shown in FIG. 1). Depending upon the particular implementation, network communication module 510 and network interface 512 may be configured to support unidirectional communication from monitor 500 to one or more network devices, unidirectional communication from one or more network devices to monitor 500, or bidirectional communication between monitor 500 and one or more network devices. Thus, network device interface 512 may be configured to receive an incoming network communication from an originating network device, and/or to enable transmission of an outgoing network communication to a receiving network device. Moreover, depending upon the particular implementation, network communication module 510 and network interface 512 may be configured to support wireless data communication, wired/cabled data communication, or both.

For wireless transmissions of network communications, network communication module 510 and network interface 512 support one or more wireless data communication protocols that are also supported by the network device(s) communicating with monitor 500. Any number of suitable wireless data communication protocols, techniques, or methodologies may be supported by monitor 500, including, without limitation, the wireless protocols listed above. In an embodiment, a wireless network interface 512 may include or be realized as hardware, software, and/or firmware, as described above for a wireless local device interface 502.

For transmissions of network communications over a cable, a wired connection, or other physical link, network communication module 510 and network interface 512 support one or more wired/cabled data communication protocols that are also supported by the network device(s) communicating with monitor 500. Any number of suitable data communication protocols, techniques, or methodologies may be supported by monitor 500, including, without limitation, the wired or cable based protocols listed above. In an embodiment, a wired/cabled network interface 512 may include or be realized as hardware, software, and/or firmware, as described above for a wired/cabled local device interface 502.

Figure 6:
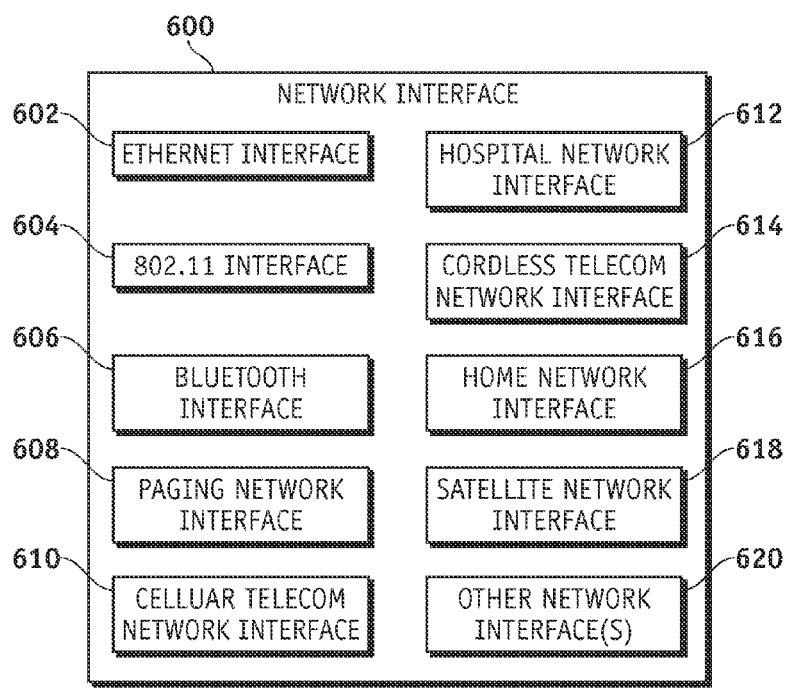
FIG. 6 is a schematic representation of a network interface suitable for use with the infusion system monitor depicted in FIG. 5.

FIG. 6 is a schematic representation of a generalized network interface 600 suitable for use with monitor 500. For ease of description, network interface 600 is depicted as a general interface that includes a number of wireless and wired/cabled data communication aspects. Network interface 600 need not include multiple interfaces as depicted in FIG. 6 and, indeed, an embodiment may utilize only one specific type of interface. Network interface 600 generally includes an Ethernet interface 602, an 802.11 interface 604, a Bluetooth interface 606, a paging network interface 608, a cellular telecommunication network interface 610, a hospital network interface 612, a cordless telecommunication network interface 614, a home network interface 616, a satellite network interface 618, and other network interfaces 620.

Ethernet interface 602 may include or be realized as hardware, software, and/or firmware that is suitably configured to cooperate with network communication module 510 to accommodate Ethernet compliant network data communications with one or more network devices. For example, Ethernet interface 602 may include a T-568A Ethernet connector, a T-568B Ethernet connector, an RJ-45 connector, or any connector that is compatible with Ethernet cables.

802.11 interface 604 may include or be realized as hardware, software, and/or firmware that is suitably configured to cooperate with network communication module 510 to accommodate 802.11 compliant network data communications with one or more network devices. For example, 802.11 interface 604 may include an appropriate radio module, an 802.11 transceiver card, an RF front end, an RF antenna, and/or 802.11 access point functionality.

Bluetooth interface 606 may include or be realized as hardware, software, and/or firmware that is suitably configured to cooperate with network communication module 510 to support Bluetooth compliant network data communications with one or more network devices. For example, Bluetooth interface 606 may include an appropriate radio module, a Bluetooth transceiver, an RF front end, and/or an RF antenna.

Paging network interface 608 may include or be realized as hardware, software, and/or firmware that is suitably configured to cooperate with network communication module 510 to support network communications in compliance with a paging network protocol. For example, paging network interface 608 may include an appropriate radio module, a transceiver card, an RF front end, and/or an RF antenna.

Cellular telecommunication network interface 610 may include or be realized as hardware, software, and/or firmware that is suitably configured to cooperate with network communication module 510 to accommodate network communications in compliance with a cellular telecommunication protocol (e.g., CDMA, GSM, or the like). For example, cellular telecommunication network interface 610 may include an appropriate radio module, a transceiver card, an RF front end, and/or an RF antenna.

Hospital network interface 612 may include or be realized as hardware, software, and/or firmware that is suitably configured to cooperate with network communication module 510 to support network communications in compliance with a hospital network protocol. In embodiments, the hospital network protocol may be a wireless data communication protocol or a wired/cabled data communication protocol. In this regard, a wireless hospital network interface 612 may include an appropriate radio module, a transceiver card, an RF front end, an RF antenna, an infrared transmitter, an infrared sensor, a magnetic induction transducer, or the like. Depending upon the particular deployment, a wireless hospital network interface 612 may be compliant with any of the other wireless/cordless data communication protocols described here. A wired/cabled hospital network interface 612 may include suitably configured connectors, sockets, jacks, plugs, or adaptors. Moreover, depending upon the particular application, a wired/cabled hospital network interface 612 may be compliant with any of the other wired/cabled data communication protocols described here.

Cordless telecommunication network interface 614 may include or be realized as hardware, software, and/or firmware that is suitably configured to cooperate with network communication module 510 to support network communications in compliance with a cordless telecommunication protocol. Such protocols are commonly used in household cordless telephone systems. In practice, cordless telecommunication network interface 614 may include an appropriate radio module, a cordless telephone base station, a transceiver card, an RF front end, and/or an RF antenna.

Home network interface 616 may include or be realized as hardware, software, and/or firmware that is suitably configured to cooperate with network communication module 510 to support network communications in compliance with a home network protocol. Such home network protocols may be utilized in the context of a home control system, a home computing network that leverages existing telephone wires or existing AC power lines, a home security or alarm system, a home entertainment system, or the like. In embodiments, the home network protocol may be a wireless data communication protocol or a wired/cabled data communication protocol. In this regard, a wireless home network interface 616 may include an appropriate radio module, a transceiver base station, a transceiver card, an RF front end, an RF antenna, an infrared transmitter, an infrared sensor, a magnetic induction transducer, or the like. Depending upon the particular deployment, a wireless home network interface 616 may be compliant with any of the other wireless/cordless data communication protocols described here. A wired/cabled home network interface 616 may include suitably configured connectors, sockets, jacks, plugs, or adaptors. Moreover, depending upon the particular application, a wired/cabled home network interface 616 may be compliant with any of the other wired/cabled data communication protocols described here.

Satellite network interface 618 may include or be realized as hardware, software, and/or firmware that is suitably configured to cooperate with network communication module 510 to accommodate network communications in compliance with a satellite data communication protocol. For example, satellite network interface 618 may include an appropriate radio module, a transceiver card, an RF front end, and/or an RF antenna. Alternatively (or additionally), satellite network interface 618 may include suitably configured connectors, sockets, jacks, plugs, or adaptors that facilitate wired/cabled connection to a separate piece of satellite network equipment, e.g., a satellite dish or a satellite transceiver module.

In practice, network interface 600 may utilize any number of network interfaces 620 other than the specific types described above. Such other network interfaces 620 can be suitably configured to support network communications in accordance with existing data communication protocols, whether publicly known or proprietary. Moreover, other network interfaces 620 enable network interface 600 to support wireless or wired data communication protocols that may be developed in the future.

Figure 7:
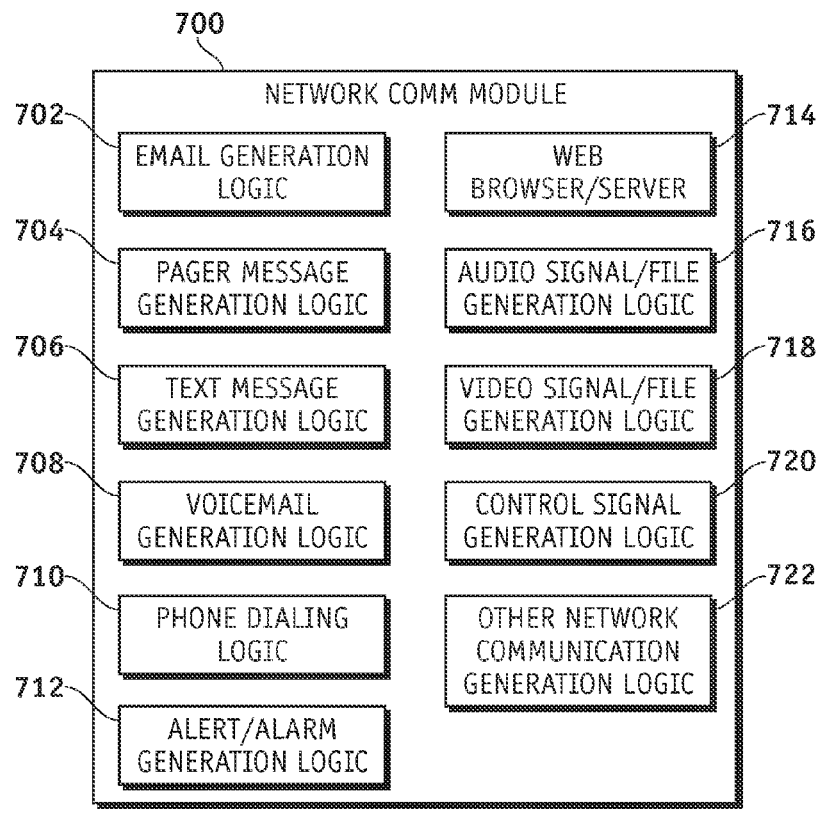
FIG. 7 is a schematic representation of a network communication module suitable for use with the infusion system monitor depicted in FIG. 5.

FIG. 7 is a schematic representation of a network communication module 700 suitable for use with monitor 500. For ease of description, network communication module 700 is depicted as a general module that includes processing logic for handling different types of network communications. In practice, network communication module 700 need not support different modes of network communications as depicted in FIG. 7 and, indeed, an embodiment may process only one specific network communication format or type. Network communication module 700 generally includes email generation logic 702, pager message generation logic 704, text message generation logic 706, voicemail generation logic 708, phone dialing logic 710, alert/alarm generation logic 712, a web browser/server 714, audio signal/file generation logic 716, video signal/file generation logic 718, control signal generation logic 720, and other network communication generation logic 722.

Email generation logic 702 may include or be realized as hardware, software, and/or firmware that is suitably configured to generate network communications as email. For example, email generation logic 702 may generate automatic or user-created email that conveys notifications, alerts, alarms, status reports, physiologic data, or other information that is intended for a destination network device. In embodiments, email generation logic 702 may be compatible with any suitable email system or technology, including web-based email systems.

Pager message generation logic 704 may include or be realized as hardware, software, and/or firmware that is suitably configured to generate network communications as pager messages. For example, pager message generation logic 704 may generate automatic or user-created pager messages that convey notifications, alerts, alarms, status reports, physiologic data, or other information that is intended for a pager device or any compatible destination network device. In embodiments, pager message generation logic 704 may be compatible with any suitable pager system or technology, including web-based paging systems.

Text message generation logic 706 may include or be realized as hardware, software, and/or firmware that is suitably configured to generate network communications as text messages. Such text messages may be carried over existing cellular telephone networks, existing pager networks, the Internet, local area networks, hospital networks, home networks, or the like. For example, text message generation logic 706 may generate automatic or user-created text messages that convey notifications, alerts, alarms, status reports, physiologic data, or other information that is intended for any compatible destination network device. In embodiments, text message generation logic 706 may be compatible with any suitable text messaging application or technology.

Voicemail generation logic 708 may include or be realized as hardware, software, and/or firmware that is suitably configured to generate network communications as voicemail messages. For example, voicemail message generation logic 708 may generate automatic or user-created voicemail messages that convey notifications, alerts, alarms, status reports, physiologic data, or other information that is intended for any compatible destination network device. In embodiments, such voicemail messages can be generated as audio files suitable for transmission as electronic attachments. Upon receipt, the destination network device can play the voicemail message using an appropriate playback mechanism, multimedia application, or the like. In embodiments, voicemail generation logic 708 may be compatible with any suitable voice messaging, telephone system, or multimedia application.

Phone dialing logic 710 may include or be realized as hardware, software, and/or firmware that is suitably configured to generate network communications as an outgoing telephone call. For example, phone dialing logic 710 may be configured to dial (automatically or in response to user interaction) an outgoing telephone number as needed to convey notifications, alerts, alarms, status reports, physiologic data, or other information that is intended for any compatible destination network device. Phone dialing logic 710 may also cooperate with one or more of the other logical components of network communication module 700, for example, voicemail generation logic 708, to facilitate transmission of certain network communications. In embodiments, phone dialing logic 710 may be compatible with any suitable telephone system or application.

Alert/alarm generation logic 712 may include or be realized as hardware, software, and/or firmware that is suitably configured to generate alerts and/or alarms intended for distribution to network devices. For example, alert/alarm generation logic 712 may generate automatic or user-created alerts or alarms that indicate any of the following, without limitation: battery status of a device within the local infusion system; when a physiologic characteristic of the patient crosses a predetermined threshold value; when a telemetered device within the local infusion system is out of range of the monitor; a scheduled calibration for a piece of equipment within the local infusion system; or any scheduled event related to the operation of the infusion system. In embodiments, alert/alarm generation logic 712 may cooperate with one or more of the other logical components of network communication module 700, for example, text message generation logic 706, to facilitate the formatting and network transmission of alerts and alarms. Upon receipt, the destination network device can generate an alert/alarm using an appropriate playback mechanism, multimedia application, an illuminating element, a speaker, or the like.

Web browser/server 714 represents a software application that is configured to generate network communications as markup language documents, e.g., HTML documents. Moreover, web browser/server 714 may include conventional web browsing capabilities that enable the monitor device to access web pages via the Internet. In this regard, web browser/server 714 may cooperate with one or more of the other logical components of network communication module 700, for example, email generation logic 702 or text message generation logic 706, to facilitate the transmission and receipt of certain network communications. Web browser applications and web server applications are well known and, therefore, will not be described in detail here.

Audio signal/file generation logic 716 may include or be realized as hardware, software, and/or firmware that is suitably configured to generate network communications as audio signals and/or audio files. The audio signals or files may be pre-programmed into the monitor device (or into the device that creates the audio signals or files). Alternatively, the audio signals or files may be created by a user of the monitor device (or by a user of the device in communication with the monitor device). For example, audio signal/file generation logic 716 may generate automatic or user-created audio signals or audio files that convey notifications, alerts, alarms, status reports, physiologic data, or other information that is intended for any compatible destination network device. Audio-based alerts/alarms may be automatically initiated by the monitor device or by a device in communication with the monitor device. Alternatively, audio-based alerts/alarms may be initiated by a user, patient, or caregiver at the monitor device or at a device in communication with the monitor device. Upon receipt, the destination network device can play the audio signals or audio files using an appropriate playback mechanism, multimedia application, or the like.

As used here, an audio signal may be a streaming audio signal, a broadcast radio signal, or a control signal that initiates the generation of audio at the destination network device, while an audio file represents a file that is received and interpreted by the destination network device (which then executes the audio file to generate audio). For example, audio signal/file generation logic 716 may be configured to generate MP3 audio files, WMA audio files, or the like. In this regard, audio signal/file generation logic 716 may cooperate with one or more of the other logical components of network communication module 700, for example, voicemail generation logic 708 or alert/alarm generation logic 712, to facilitate the transmission and receipt of certain network communications.

Video signal/file generation logic 718 may include or be realized as hardware, software, and/or firmware that is suitably configured to generate network communications as video signals and/or video files. The video signals or files may be pre-programmed into the monitor device (or into the device that creates the audio signals or files). Alternatively, the video signals or files may be created by a user of the monitor device (or by a user of the device in communication with the monitor device). For example, video signal/file generation logic 718 may generate automatic or user-created video signals or video files that convey notifications, alerts, alarms, status reports, physiologic data, or other information that is intended for any compatible destination network device. Video-based alerts/alarms may be automatically initiated by the monitor device or by a device in communication with the monitor device. Alternatively, video-based alerts/alarms may be initiated by a user, patient, or caregiver at the monitor device or at a device in communication with the monitor device. Upon receipt, the destination network device can play the video signals or video files using an appropriate playback mechanism, multimedia application, or the like.

As used here, a video signal may be a streaming video signal, a broadcast video signal, or a control signal that initiates the generation of video at the destination network device, while a video file represents a file that is received and interpreted by the destination network device (which then executes the video file to generate video). For example, video signal/file generation logic 718 may be configured to generate MPEG video files, JPG image files, or the like. In this regard, video signal/file generation logic 718 may cooperate with one or more of the other logical components of network communication module 700, for example, alert/alarm generation logic 712, to facilitate the transmission and receipt of certain network communications.

Control signal generation logic 720 may include or be realized as hardware, software, and/or firmware that is suitably configured to generate network communications as control signals for the receiving network device. For example, control signal generation logic 720 may generate automatic or user-created control signals that initiate the generation of notifications, alerts, alarms, displays, or otherwise control the operation of any compatible destination network device. Upon receipt of such a control signal, a destination network device will respond in a suitable manner—activating a display, activating a vibrating element, activating an illumination element, generating an audio or video response, or the like. In embodiments, control signal generation logic 720 may cooperate with one or more of the other logical components of network communication module 700, for example, alert/alarm generation logic 712, to facilitate the formatting and network transmission of control signals.

In practice, network communication module 700 may utilize other network communication generation logic 722 in lieu of, or in addition to, the specific types described above. Such other logical components can be suitably configured to generate network communications in various existing formats, whether publicly known or proprietary. Moreover, such other logical components enable network communication module 700 to support additional formats that may be developed in the future.

Figure 8:
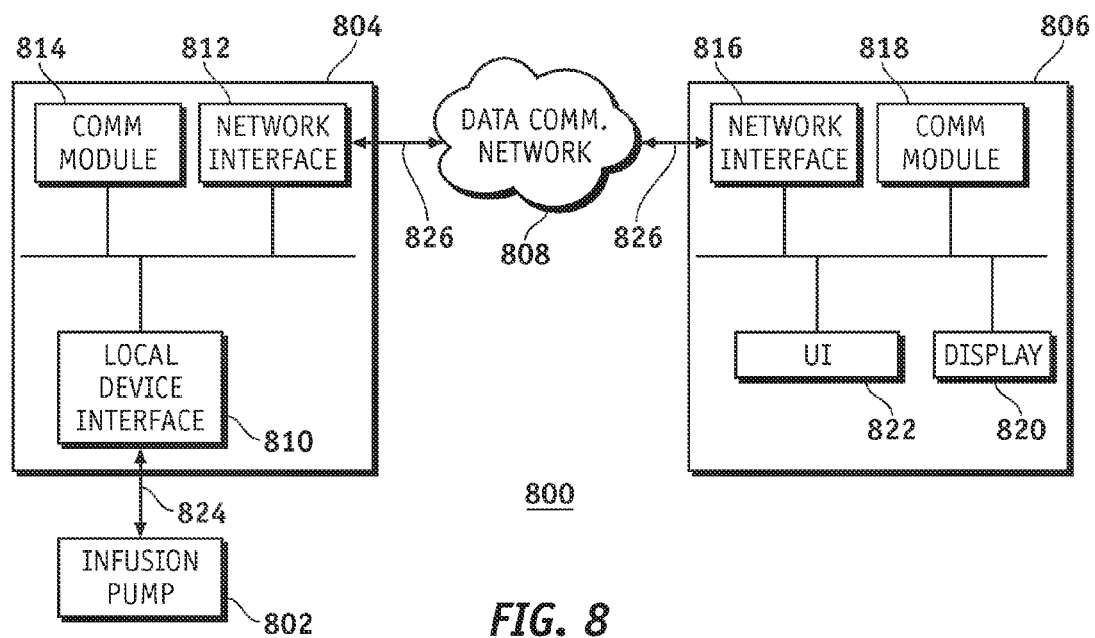
FIG. 8 is a schematic representation of a network-based infusion system configured in accordance with an example embodiment of the invention.

FIG. 8 is a schematic representation of a network-based medical device system 800 configured in accordance with an example embodiment of the invention. System 800 represents one simple implementation of a system that might utilize some of the devices, techniques, and methodologies described here. A vast number of alternative configurations may be constructed and operated within the scope of the invention. For example, although system 800 is described below in the context of an infusion pump, the infusion pump is not a requirement for embodiments of the invention.

Network-based infusion system 800 generally includes an infusion pump 802, a monitor device 804 (or any suitable local device that is defined to be within a local infusion system), and a network device 806. In this example embodiment, monitor device 804 and network device 806 communicate with each other via any number of network communication links established in a data communication network 808. Moreover, although not a requirement, FIG. 8 depicts bidirectional communications between monitor device 804 and network device 806. Network device 806 may be, for example, a network-based monitor, a networked computer, a cellular telephone or other mobile computing device, any network device 104 described in connection with FIG. 1, or any network-based device described elsewhere. Data communication network 808 may be (or include), for example, the Internet, a cellular telecommunication network, a paging system network, a local or wide area network, any wireless or wired network described in connection with FIG. 1, or any network described elsewhere.

As described in more detail in connection with FIG. 5, monitor 804 may include a local device interface 810, a network interface 812, and one or more suitable communication modules 814 (e.g., a local communication module and/or a network communication module). Network device 806 may include a network interface 816, which is configured for compatibility with network interface 812, one or more suitably configured communication modules 818, a display element 820, and user interface features 822. Network interface 816 may be configured as described above in connection with network interface 512 and in connection with network interface 600. Communication module(s) 818 may be configured as described above in connection with network communication module 510 and in connection with network communication module 700. Communication module(s) 818 are configured to enable network device 806 to receive, process, and interpret network communications received from monitor device 804. In addition, communication module(s) 818 may be configured to enable network device 806 to process, generate, and transmit outgoing network communications intended for monitor device 804. User interface features 822 and display element 820 enable a user of network device 806 to remotely view data that might be displayed at infusion pump 802 or monitor device 804, remotely control monitor device 804 or infusion pump 802, and/or remotely program or modify operating parameters of monitor device 804 or infusion pump 802.

In some embodiments of network-based infusion system 800, infusion pump 802 and monitor device 804 communicate using a first data communication protocol, while monitor device 804 and network device 806 communicate using a second data communication protocol (or a combination of protocols). Local communications between infusion pump 802 and monitor device 804 are carried over one or more local communication links 824, which may be wireless or wired. Network communications between monitor device 804 and network device 806 are carried over one or more network communication links 826, which may be wireless or wired.

For example, infusion pump 802 may transmit local communications (such as pump status information) to monitor device 804, where the local communications are transmitted in accordance with a Bluetooth data communication protocol. Moreover, infusion pump 802 may receive incoming data from monitor device 804 using the same Bluetooth protocol. In contrast, monitor device 804 may transmit network communications (such as pump status information, alerts, or patient data) to network device 806, where the network communications are transmitted in accordance with a cellular telecommunication protocol such as CDMA. Similarly, monitor device 804 may receive incoming data from network device 806 using the same CDMA protocol.

FIG. 9 is a flow chart that depicts an example network-based medical device system monitoring process 900. The various tasks performed in connection with process 900 may be performed by software, hardware, firmware, or any combination. For illustrative purposes, the following description of process 900 may refer to elements mentioned above in connection with FIGS. 1-8. In embodiments, portions of process 900 may be performed by different elements of the described system, e.g., a network device or a functional element or operating component. It should be appreciated that process 900 may include any number of additional or alternative tasks, the tasks shown in FIG. 9 need not be performed in the illustrated order, and process 900 may be incorporated into a more comprehensive procedure or process having additional functionality not described in detail here.

Monitoring process 900 may be performed by a network device that is external to a local infusion system having an infusion pump that controls the infusion of fluid into the body of a user. Process 900 may begin when the network device receives (task 902) a network communication that conveys pump data associated with the local infusion pump. The network communication may be generated by (or originate at) any transmitting device within the local infusion system, such as a bedside monitor device, a hospital monitor device, a physiological characteristic meter, a remote controller, a handheld monitor/controller, the infusion pump itself, or the like. The pump data may include any information or content related to the operation, control, programming, or status of the infusion pump and/or the transmitting device, including, without limitation: physiologic data of the user/patient, alarms, alerts, graph or chart data, a basal rate of fluid delivered by the infusion pump, bolus information for a bolus of fluid delivered by the infusion pump, or any suitably formatted text, audio, or visual information. As described above in connection with FIG. 5 and FIG. 6, the network device may receive the network communication in compliance with one or more appropriate data communication protocols, including, without limitation: an Ethernet protocol, an IEEE 802.11 protocol (any variant), a Bluetooth protocol, a paging network protocol, a cellular telecommunication protocol (e.g., CDMA or GSM), a cordless telecommunication protocol, a home network data communication protocol, a satellite data communication protocol, a hospital network protocol, or any suitable wireless or wired/cabled data communication protocol that enables the network device to receive network communications via a wireless, cabled, and/or wired communication link.

In practice, the network device processes the received network communication and extracts (task 904) the pump data from the network communication. Task 904 may be performed by a suitably configured communication module and/or a suitably configured processing architecture resident at the network device. In response to such processing, the network device may generate (task 906) indicia of the pump data for display, playback, broadcast, or rendering at the network device. In connection with task 906, the network device may: generate indicia of received physiologic data; generate indicia of local device status information; generate indicia of an alert or an alarm; generate indicia of a basal rate of fluid delivery; generate indicia of bolus information; or the like. In embodiments, the network device may generate indicia of the pump data in any suitable manner, including, without limitation: generating an audible representation of the pump data, such as an audible alarm, alert, recording, or audio signal; generating a visual representation of the pump data, such as a graph or a text display; activating an illumination element of the network device, e.g., an indicator light or a flashing display screen; or activating a vibration element of the network device.

Monitoring process 900 assumes that the network device can transmit network communications back to a device within the local infusion system. In this regard, process 900 may select or determine (task 908) one or more data communication protocols corresponding to a local device within the infusion system. Task 908 may be performed to ensure that the network device utilizes an appropriate protocol for compatible communication with the local device. The network device may also obtain or generate an instruction or programming parameter intended for the infusion pump or another local device within the infusion system. Such instructions or programming parameters may be generated by the network device or obtained from an operator of the network device. The network device may be configured to generate (task 910) a suitably configured control communication that conveys the instruction or programming parameter. Depending upon the particular system deployment and the specific operating conditions, an example control communication may include, without limitation: an alert disable instruction; an activation instruction for the infusion pump or any local device; a programming parameter for the infusion pump or any local device; or the upload of software programs (main application code or auxiliary function code such as motor control, RF telemetry code, or the like). Eventually, the network device can transmit (task 912) the control communication in an appropriate format and in compliance with the particular data communication protocol utilized for the communication session with the local device. Upon receipt, the receiving local device can process the control communication in an appropriate manner.

In alternate embodiments of the invention, monitoring process 900 can be modified for use in connection with a medical device system that does not include an infusion pump. For example, the tasks of process 900 may be performed in an equivalent manner to receive and process a network communication that conveys patient data, monitor data, or other medical device information that might originate at a device within the local system, and such data need not include pump data.

FIG. 10 is a flow chart that depicts an example network-based medical device system communication process 1000. The various tasks performed in connection with process 1000 may be performed by software, hardware, firmware, or any combination of these. For illustrative purposes, the following description of process 1000 may refer to elements mentioned above in connection with FIGS. 1-8. In embodiments, portions of process 1000 may be performed by different elements of the described system, e.g., a local device within an infusion system or a functional element or operating component. It should be appreciated that process 1000 may include any number of additional or alternative tasks, the tasks shown in FIG. 10 need not be performed in the illustrated order, and process 1000 may be incorporated into a more comprehensive procedure or process having additional functionality not described in detail here.

Network communication process 1000 may be performed by a transmitting device that is within a local medical device system, e.g., an infusion system having an infusion pump that controls the infusion of fluid into the body of a user. For example, the transmitting device may be any local device within the local infusion system, such as a bedside monitor device, a hospital monitor device, a physiological characteristic meter, a physiological characteristic sensor transmitter, a remote controller, a handheld monitor/controller, the infusion pump itself, or the like. Process 1000 may begin when the transmitting device obtains (either internally, from another device, or from a user) or generates a notification (task 1002) related to the operation of the infusion pump and/or related to the operation of another local device. As used here, a notification may be any signal, alert, alarm, content, data, or information that is intended to be forwarded to another device, or is utilized as a prompt or a trigger to invoke a response by the transmitting device.

Network communication process 1000 may select or determine (task 1004) an external receiving device, which will be a network device in this example, that represents the intended recipient of the notification. In addition, process 1000 may select or determine (task 1006) one or more data communication protocols corresponding to the intended external receiving device. Task 1006 may be performed to ensure that the local transmitting device utilizes an appropriate protocol for compatible communication with the network device. As described above in connection with FIG. 5 and FIG. 6, the local device may transmit network communications in compliance with one or more appropriate data communication protocols, including, without limitation: an Ethernet protocol, an IEEE 802.11 protocol (any variant), a Bluetooth protocol, a paging network protocol, a cellular telecommunication protocol (e.g., CDMA or GSM), a cordless telecommunication protocol, a home network data communication protocol, a satellite data communication protocol, a hospital network protocol, or any suitable wireless or wired/cabled data communication protocol that enables the local device to transmit network communications via a wireless, cabled, and/or wired communication link.

The local transmitting device may then generate (task 1008) a network communication that conveys the notification, where the network communication is compatible with the selected data communication protocol. In accordance with embodiments, the network communication may include any information or content related to the operation, control, programming, or status of the infusion pump and/or the transmitting device, including, without limitation: physiologic data of the user/patient, alarms, alerts, graph or chart data, a basal rate of fluid delivered by the infusion pump, bolus information for a bolus of fluid delivered by the infusion pump, or any suitably formatted text, audio, or visual information. As described above in connection with FIG. 7, the network communication may be formatted as (or include) different message types, file types, or signal types, including, without limitation: an email message; a pager message; a text message; a voicemail message; an outgoing telephone call to the receiving network device; a markup language document, such as a web page; an audio signal; an audio file; a video signal; or a video file.

Eventually, the local transmitting device transmits (task 1010) the network communication to the external receiving device. The local device transmits the network communication in accordance with the network data communication protocol selected during task 1006. In one example, the network communication is conveyed in an outgoing telephone call, and the local transmitting devices transmits the network communication by initiating an outgoing telephone call to the destination network device. In other example embodiments, task 1010 represents the transmission of a message, file, and/or signal having a specified type and format. Upon receipt of the network communication, the destination network device can process the notification in an appropriate manner.

Figure 11:
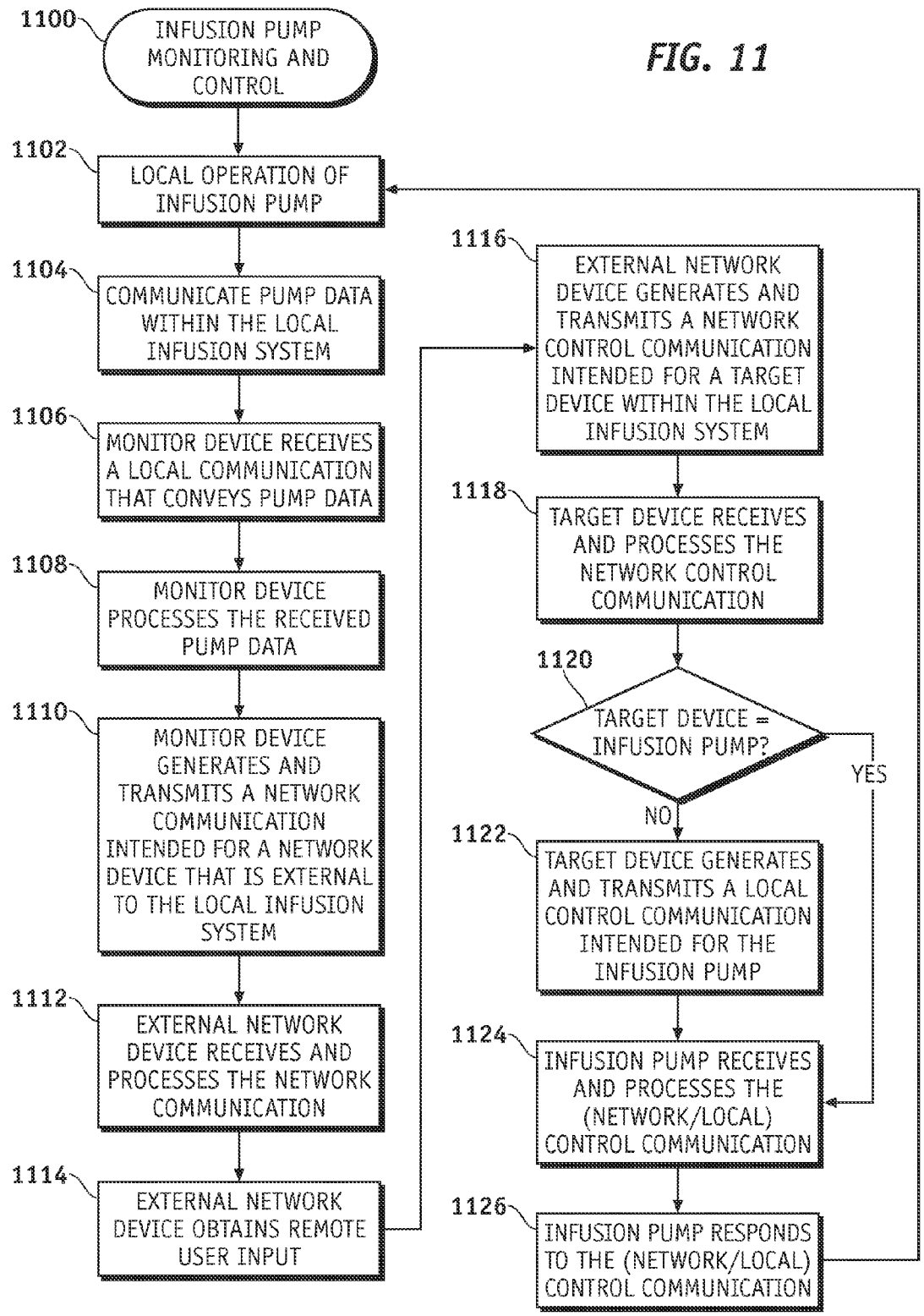
FIG. 11 is a flow chart that depicts an example network-based infusion pump monitoring and control process.

In alternate embodiments of the invention, process 1000 can be modified for use in connection with a medical device system that does not include an infusion pump. For example, the tasks of process 1000 may be performed in an equivalent manner to process and transmit a network communication that conveys patient data, monitor data, or other medical device information that might originate at a device within the local system, and such information need not include pump data FIG. 11 is a flow chart that depicts an example network-based infusion pump monitoring and control process 1100. Process 1100 represents one example technique for operating a network-based infusion pump system. A system may be able to support any number of alternative techniques and methodologies, and the following description of process 1100 is not intended to limit the scope or application of the invention in any way. The various tasks performed in connection with process 1100 may be performed by software, hardware, firmware, or any combination. For illustrative purposes, the following description of process 1100 may refer to elements mentioned above in connection with FIGS. 1-8. In embodiments, portions of process 1100 may be performed by different elements of the described system, e.g., a local device, an infusion pump, a network device or any functional element or operating component. It should be appreciated that process 1100 may include any number of additional or alternative tasks, the tasks shown in FIG. 11 need not be performed in the illustrated order, and process 1100 may be incorporated into a more comprehensive procedure or process having additional functionality not described in detail here.

Infusion pump monitoring and control process 1100 is performed in conjunction with the normal local operation of an infusion pump (task 1102). Process 1100 preferably supports the communication of pump data within the local infusion system (task 1104), as described in detail above. In particular, task 1104 may correspond to the transmission of pump data from the infusion pump to a monitor device within the local infusion system, the transmission of pump data between local devices other than the infusion pump, or the like. In this example, a local monitor device receives a local communication that conveys pump data (task 1106). The local monitor device may be a bedside monitor, a hospital monitor, a handheld monitor/controller, or any suitably configured local device as described above. If necessary, the local monitor device processes the received pump data (task 1108) to determine how best to respond.

In this example, the local monitor device generates and transmits a network communication in response to the received pump data (task 1110). The network communication may be intended for any compatible network device that is external to the local infusion system. As described above, the network communication is preferably generated in accordance with a selected network data communication protocol that is also supported by the destination network device. Infusion pump monitoring and control process 1100 assumes that the external network device receives and processes (task 1112) the network communication in an appropriate manner.

For example, the network device may generate an alert or an alarm that originated at the infusion pump.

In response to the network communication (e.g., an alert in this example), the network device may obtain a remote user input (task 1114). In this regard, a remote user input may correspond to manipulation of user interface features located at the network device. For example, the user of the network device may elect to disable the alert by engaging a "DISABLE" button on the network device. As another example, the user of the network device may elect to remotely administer a bolus by engaging an "ACTIVATE" button on the network device. In response to the remote user input, the network device may generate and transmit (task 1116) a suitably configured network control communication that is intended for a target device within the local infusion system. This control communication is formatted for compliance with a particular data communication protocol that is also supported by the target device. The target device may, but need not be, the same local device that transmitted (or originated) the local communication received during task 1106.

Infusion pump monitoring and control process 1100 assumes that the intended target device receives and processes (task 1118) the network control communication in an appropriate manner. Generally, the target device processes the received control communication to determine how best to respond. If the target device is the infusion pump, then process 1100 may proceed to a task 1124. If not, then process 1100 may proceed to a task 1122. During task 1122, the target device may generate and transmit a local control communication that is intended for the infusion pump. The target device generates and transmits the local control communication in accordance with a data communication protocol that is supported within the local infusion system. As an example, task 1122 can be performed when the target device is a local monitor device that locally communicates with the infusion device. Eventually, the infusion pump receives and processes (task 1124) the network or local control communication in an appropriate manner. In this regard, task 1124 is performed in response to the remote user input obtained at the network device during task 1114. In embodiments, the local infusion pump will respond to the control communication (task 1126) in a suitable manner. For example, the infusion pump may react in the following manner, without limitation: disable an alarm or an alert; update its software or firmware; modify its basal rate; activate its pump to administer a bolus; generate a local alert/alarm; perform a calibration routine; or the like.

In this example embodiment, infusion pump monitoring and control process 1100 enables continuous or periodic monitoring and control of the infusion pump. Accordingly, FIG. 11 depicts process 1100 as a loop, where task 1126 leads back to task 1102 for purposes of continued local operation of the infusion pump.

FIGS. 12-17 are screen shots that may be generated by monitor devices, controller devices, network devices, display devices, and/or other infusion system devices configured in accordance with example embodiments of the invention. For example, the content of these screen shots may be displayed by bedside monitor 200 (see FIG. 2), by hospital monitor 300 (see FIG. 3), by handheld monitor/controllers 400 and 410 (see FIG. 4), by any of the local devices within local infusion system 102 (see FIG. 1), and/or by any of the network devices 104 utilized by network-based infusion system 100 (see FIG. 1).

Figure 12:
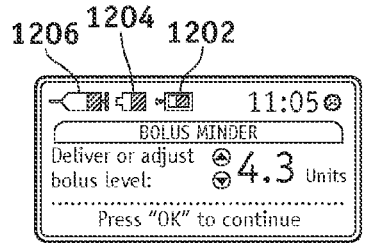
FIGS. 12-17 are screen shots that may be generated by monitor devices, controller devices, network devices, display devices, and/or other infusion system devices configured in accordance with example embodiments of the invention.

FIG. 12 is a screen shot that is suitable for use with a relatively small device, such as a handheld monitor, a personal digital assistant, a wireless phone, a key fob remote control, or the like. This screen shot includes a clock display, an RF quality indicator 1202, a battery indicator 1204, a fluid level indicator 1206 that represents the amount of fluid remaining in the infusion pump, and a recommended bolus (4.3 units in this example). This screen shot also includes the prompt: "Press 'OK' to Continue". The user can press "OK" to display other options, such as an activation request that controls the infusion pump to administer the recommended bolus.

Figure 13:
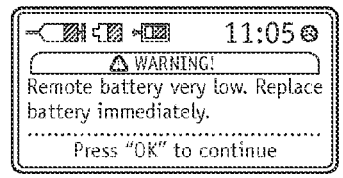

FIG. 13 is another screen shot that is suitable for use with a relatively small device. This screen shot includes a warning display, which may be accompanied by a suitably generated alert or alarm. Here, the warning includes text that indicates a low battery condition and a reminder to replace the battery. In example embodiments of the invention, such a warning may be associated with the battery in the device that actually displays the warning, or it may be associated with the battery in a remote device being monitored by the device that actually displays the warning. In this regard, this screen shot may be displayed at a network monitor device, where the low battery warning indicates that the battery in the local infusion pump device is low.

Figure 14:
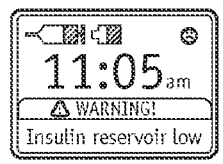

FIG. 14 is a screen shot that is suitable for use with a small form factor device, such as a remote control, a watch sized monitor, a portable display-only device, or the like. This screen shot includes a clock display, which is proportionately large for readability. This screen shot also includes a warning display, which may be accompanied by a suitably generated alert or alarm. Here, the warning includes text that indicates a low insulin reservoir condition for the monitored infusion pump. In example embodiments, this screen shot can be displayed on the infusion pump itself, on a remote device within the local infusion system, and/or on a network-based monitoring device.

Figure 15:
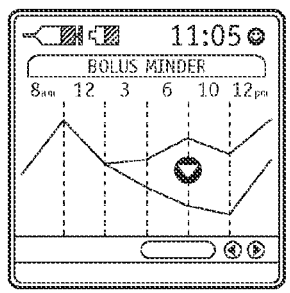
Figure 16:
Figure 17:
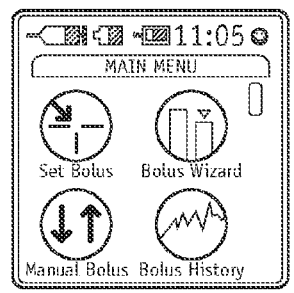

FIGS. 15-17 are various screen shots that are suitable for use with a relatively small device, such as a personal digital assistant, a wireless phone, or a pager device. The example screen shot of FIG. 15 includes historical BG data for the patient, rendered in a graph format, and a clock display. The screen shot of FIG. 16 includes a warning related to a low level in the insulin reservoir of the insulin pump, along with a clock display. The screen shot of FIG. 17 represents a "Main Menu" display for the device, where the menu includes a number of options for the user. For example, the device may display selectable menu icons, including, without limitation: a "Set Bolus" icon; a "Bolus Wizard" icon; a "Manual Bolus" icon; and a "Bolus History" icon. Selection of a given icon may cause the device to generate a new display screen that provides additional information or options related to the selected feature or function. For example, the "Set Bolus" icon enables the user to program the device for a specific bolus value or values that can be activated during use; the default values could be assigned to correspond to various meal carbohydrate values commonly consumed by the user, the "Bolus Wizard" icon launches a feature that enables the user to calculate a bolus of insulin that is appropriate for the patient's current condition, the "Manual Bolus" icon enables the user to deviate from the default bolus value(s), and the "Bolus History" icon launches a display (such as a graph, a chart, or a report) of past bolus deliveries by the infusion pump.

Again, the specific display formats, screen shot contents, display menu trees, and other display characteristics and features may vary depending upon the particular device configuration, whether the device is a network device or a local device within the infusion system, and/or whether the device is a wireless device. The example screen shots depicted in the various figures are not intended to limit or restrict the scope or application of any embodiment of the invention.

Figure 18:
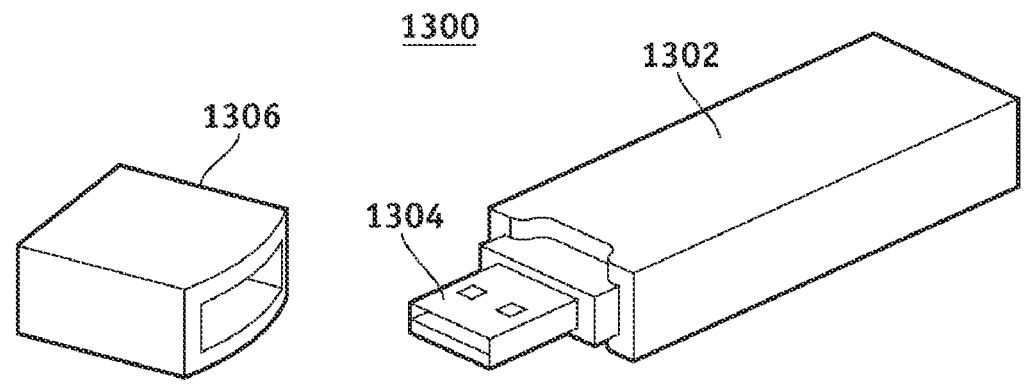
FIG. 18 is a perspective view of a data communication translation device configured in accordance with an example embodiment of the invention.

As mentioned above with regard to network-based infusion system 100 (see FIG. 1), a data communication translation device 113 may be utilized to facilitate communication between a wireless local device and a network device 104, such as a personal computer, a networked hospital computer, a caregiver office computer, or the like. FIG. 18 is a perspective view of a data communication translation device 1300 configured in accordance with one possible embodiment of the invention. In this embodiment, translation device 1300 is a relatively small and portable device that provides wireless bridge and memory storage functionality. Translation device 1300 may be conveniently sized such that it can be easily carried by a patient or a caregiver. In certain embodiments, translation device 1300 is small enough to be carried in a pocket.

Translation device 1300 includes a housing 1302 that encloses a number of functional components that are described in more detail below. This example embodiment includes a universal serial bus ("USB") connector 1304 that serves as a network interface port for translation device 1300. The network interface port can alternately be a IEEE 1394 port, a serial port, a parallel port, or the like. USB connector 1304 is configured for physical and electrical compliance with known USB specifications; such specifications will not be described in detail herein. Alternate embodiments may utilize different network interface configurations and, therefore, different network interface connectors, ports, couplers, or the like. USB connector 1304 is merely one suitable implementation of such a network interface, and embodiments of the invention are not limited to USB deployments.

Translation device 1300 may also include a removable cover 1306 that protects USB connector 1304 when translation device 1300 is not connected to a network device. Cover 1306 may be designed to snap onto USB connector 1304 and/or housing 1302 in a manner that allows the user to remove and replace cover 1306 by hand.

Figure 19:
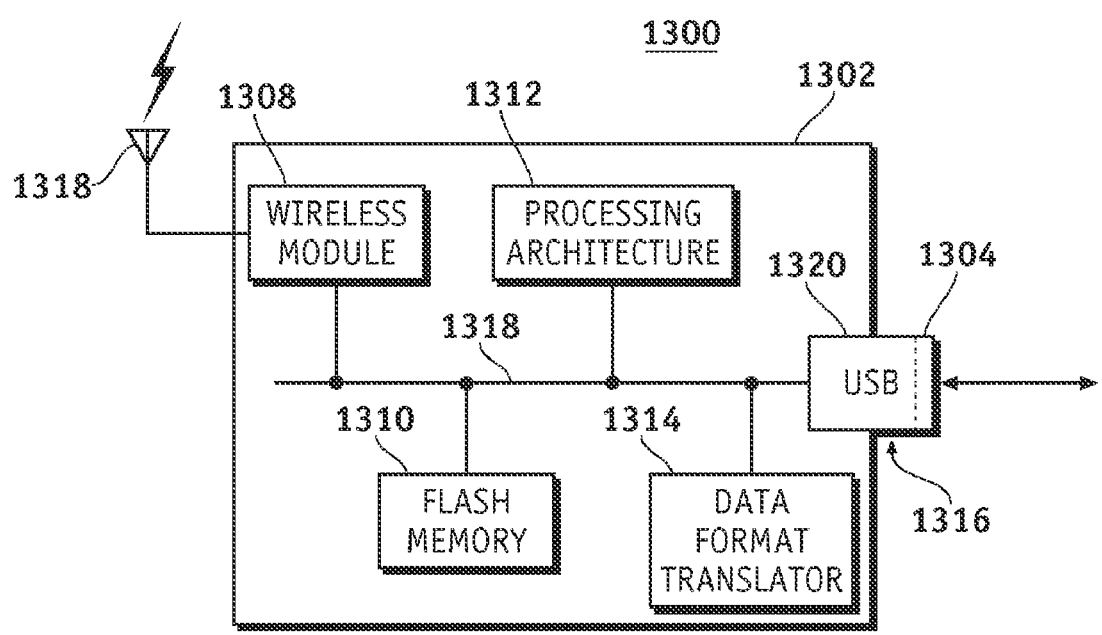
FIG. 19 is a schematic representation of a data communication translation device configured in accordance with an example embodiment of the invention.

FIG. 19 is a schematic representation of one example embodiment of translation device 1300. In this example, translation device 1300 generally includes housing 1302, a network interface port (e.g., USB connector 1304), a wireless communication module 1308, a memory element 1310, a processing architecture 1312, a data format translator 1314, and a network interface 1316 (e.g., a USB interface). The elements of translation device 1300 may be coupled together via a bus 1318 or any suitable interconnection architecture. In example embodiments, housing 1302 encloses wireless communication module 1308, memory element 1310, processing architecture 1312, and data format translator 1314. Depending upon the particular implementation, housing 1302 may also enclose at least a portion of network interface 1316.

Processing architecture 1312 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor may be realized as a microprocessor, a controller, a microcontroller, or a state machine. Moreover, a processor may be implemented as a combination of computing devices, e.g., a combination of a digital signal processor and a microprocessor, a plurality of microprocessors, one or more microprocessors in conjunction with a digital signal processor core, or any other such configuration. In an example embodiment of translation device 1300, data format translator 1314 may be implemented in processing architecture 1312 (even though FIG. 19 depicts the two as separate logical elements).

In practice, processing architecture 1312 is configured to support the various tasks, functions, and operations of translation device 1300. For example, processing architecture 1312 may be suitably configured to interpret and process incoming information, data, and content that is conveyed in local communications received from a transmitting device within the local infusion system. Likewise, processing architecture 1312 may be suitably configured to interpret and process incoming information, data, and content that is conveyed in network communications received from a network device external to the local infusion system. Processing architecture 1312 may also be configured to manage storage and retrieval of data in memory element 1310. Moreover, processing architecture 1312 may be configured to process data in response to instructions received from a network device via network interface 1316 and/or in response to instructions received from a local device via wireless communication module 1308.

In one embodiment, memory element 1310 can be a powered memory arrangement that utilizes a backup battery to maintain its storage ability. In the example embodiment, memory element 1310 is realized as nonvolatile flash memory having a suitable amount of storage capacity. The design and configuration of flash memory, its selection circuitry, and its program/erase control circuitry are generally known, and such conventional aspects of memory element 1310 will not be described in detail here. In alternate embodiments, memory element 1310 may utilize EEPROM memory, random access memory, registers, a small scale hard disk, a removable media, or the like. In this regard, memory element 1310 can be coupled to processing architecture 1312 such that processing architecture 1312 can read information from, and write information to, memory element 1310. In the alternative, memory element 1312 and processing architecture 1312 may be realized as an integrated unit. As an example, processing architecture 1312 and memory element 1310 may reside in an ASIC. As described in more detail below, memory element 1310 can be utilized to store data conveyed in wireless signals received from a local device within an infusion system. In addition, memory element 1310 can be utilized to store data conveyed in network communication signals received from a network device external to the infusion system. Such data may include local device status data, physiologic data of the user, sensor data, alerts/alarms, control data from the network device, operating instructions for translation device 1300, any of the local data types or content described herein, and/or any of the network data types or content described herein.

Wireless communication module 1308 is suitably configured to support wireless data communication with a device within an infusion system, e.g., any of the local devices mentioned in the above description of infusion system 100 (see FIG. 1). For example, the local device may be an infusion pump or a monitor device for an infusion pump. Depending upon the particular implementation, wireless communication module 1308 may be configured to support unidirectional communication from local devices, or bidirectional communication between translation device 1300 and local devices. Thus, wireless communication module 1308 may be configured to receive local communication signals from a transmitting device within the local infusion system, and/or to transmit local communication signals to a receiving device within the local infusion system.

Wireless communication module 1308 may include or be realized as a radio module that supports one or more wireless data communication protocols and one or more wireless data transmission schemes. In an embodiment, wireless communication module 1308 may include or be realized as hardware, software, and/or firmware, such as an RF front end, a suitably configured radio module (which may be a stand alone module or integrated with other or all functions of translation device 1300), a wireless transmitter, a wireless receiver, a wireless transceiver, an infrared sensor, an electromagnetic transducer, or the like. In this example, translation device 1300 includes an antenna 1318 coupled to wireless communication module 1308. Antenna 1318, which may be located inside or outside of housing 1302 (or partially inside and partially outside of housing 1302), is appropriately configured in accordance with the particular design of wireless communication module 1308.

For wireless transmissions of local communications, wireless communication module 1308 supports one or more wireless data communication protocols that are also supported by the local device(s) communicating with translation device 1300. Any number of suitable wireless data communication protocols, techniques, or methodologies may be supported by wireless communication module 1308 and translation device 1300, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB.

Network interface 1316 is generally configured to support transmission of network communications between translation device 1300 and one or more network devices. Network interface 1316 may include interface logic 1320 and network interface port 1304. Interface logic 1320 may be implemented in processing architecture 1312 (even though FIG. 19 depicts the two as separate logical elements). In this example embodiment, network interface 1316 is a USB interface, interface logic 1320 is compatible with USB specifications and requirements, and network interface port 1304 is a USB port or connector. As mentioned above, however, alternate embodiments may utilize different network interface configurations (for example, IEEE 1394) and, therefore, different network interface connectors, ports, couplers, or the like.

Network interface 1316 is suitably configured to support data communication with a device external to the infusion system, e.g., any of the network devices 104 mentioned in the above description of infusion system 100 (see FIG. 1). For example, the network device may be a personal computer having a suitable host application that can be manipulated to manage communication with translation device 1300. The personal computer may be owned by the patient, located in a caregiver facility, located in a hospital, located in a device manufacturer facility, or elsewhere. In example embodiments, the host application may be realized as software that is designed to provide monitoring, diagnostic services, patient data analysis, medical device programming, and/or other functions associated with one or more devices within the local infusion system. Depending upon the particular implementation, network interface 1316 may be configured to support unidirectional communication from translation device 1300, or bidirectional communication between translation device 1300 and network devices. Thus, network interface 1316 may be configured to receive network communication signals from a transmitting network device, and/or to transmit network communication signals to a receiving network device.

For transmission of network communication signals over a cable, a wired connection, a direct connection, or other physical link, network interface 1316 supports one or more wired/cabled data communication protocols that are also supported by the network device(s) communicating with translation device 1300. Any number of suitable data communication protocols, techniques, or methodologies may be supported by network interface 1316 and translation device 1300, including, without limitation: Ethernet; home network communication protocols; USB; IEEE 1394 (Firewire); hospital network communication protocols; and proprietary data communication protocols.

For wireless transmission of network communication signals, network interface 1316 supports one or more wireless data communication protocols that are also supported by the network device(s) communicating with translation device 1300. Any number of suitable wireless data communication protocols, techniques, or methodologies may be supported by network interface 1316 and translation device 1300, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB.

In connection with wireless data transmissions, translation device 1300 may be configured to perform dynamic frequency hopping to optimize its operation, to conserve battery life for battery-powered wireless devices, and/or to provide flexibility in the complexity of the devices with which it communicates. For example, wireless communication module 1308 may be designed to dynamically accommodate 5-channel (low power) devices and 50-channel (high power) devices. In this context, translation device 1300 may utilize a low power mode to conserve battery power when a high quality wireless link has been established. On the other hand, translation device 1300 may switch to a high power mode in response to increased packet loss, increased collision, or a generally poor quality of service.

In connection with wireless data transmissions, translation device 1300 may also be configured to support a retry periodicity for synchronous links having a designated transmission periodicity. For example, during normal operation, a synchronous wireless link may communicate one packet per minute. Translation device 1300 can be configured to initiate a retry procedure in response to a missed packet. In this regard, translation device 1300 can support retry transmissions (i.e., retransmission of the missed packet) that occur at a higher rate than the normal operating mode. For example, retry packet transmissions may occur every 20 seconds rather than once a minute. In practice, translation device 1300 and the wireless device may adapt their frequency hopping scheme to accommodate the retry packets, and resume their normal frequency hopping scheme thereafter.

Data format translator 1314, which may be realized as hardware, software, firmware, or any combination thereof, is suitably configured to reformat data between wireless communication module 1308 and network interface 1316.

Depending upon the particular implementation, such reformatting may occur for data received via wireless communication module 1308, for data received via network interface 1316, or both. For example, it may be desirable for translation device 1300 to receive a wireless communication signal at wireless communication module 1308, extract data from the wireless communication signal, and process the extracted data in an appropriate manner such that the extracted data can be conveyed in a network communication signal to be provided by network interface 1316. Likewise, it may be desirable for translation device 1300 to receive a network communication signal at network interface 1316, extract data from the network communication signal, and process the extracted data in an appropriate manner such that the extracted data can be conveyed in a wireless communication signal to be provided by wireless communication module 1308.

Translation device 1300 may be configured to encrypt data between wireless communication module 1308 and network interface 1316. Encrypting data may be desirable for ensure that confidential or sensitive information remains protected. In this example, data format translator 1314 may be configured to perform data encryption using one or more known or proprietary encryption schemes. Alternatively, translation device 1300 may include a separate encryption engine or module that performs the data encryption. Depending upon the specific implementation, data encryption may be applied to the extracted data (or any portion thereof), to the sensitive/confidential data (or any portion thereof), and/or to the entire communication signal (or any portion thereof).

Translation device 1300 provides a wireless bridge between a local device and a network device, and translation device 1300 can support a range of data transmission and data storage features. In this regard, FIG. 20 is a flow chart that depicts an example data storage and translation process 1400 that may be supported by translation device 1300. The various tasks performed in connection with process 1400 may be performed by software, hardware, firmware, or any combination. For illustrative purposes, the following description of process 1400 may refer to elements mentioned above in connection with FIGS. 18 and 19. In practice, portions of process 1400 may be performed by different elements of the described system, e.g., wireless communication module 1308, memory element 1310, processing architecture 1312, or network interface 1316. It should be appreciated that process 1400 may include any number of additional or alternative tasks, the tasks shown in FIG. 20 need not be performed in the illustrated order, and process 1400 may be incorporated into a more comprehensive procedure or process having additional functionality not described in detail here.

Data storage and translation process 1400 may begin when the translation device is attached to a network device via the network interface of the translation device (task 1402). In this example, task 1402 is associated with the coupling of a USB-compatible translation device to a personal computer via the USB interface of the translation device. In response to this attachment, process 1400 powers the translation device and initializes the wireless communication module (task 1404). In accordance with conventional methodologies, the USB interface provides operating power from the computer to the translation device, and such operating power may be utilized to energize the wireless communication module and other functional elements of the translation device. In this example, the computer detects the mounting of the translation device and responds by automatically launching its host application (task 1406). Alternatively, the computer may prompt the user to manually launch the host application.

The translation device may be configured to support an auto-detect or standby mode, during which the translation device "listens" for compatible local devices that come within wireless transmission range. Such an auto device detection mode may be desirable to enable the system to accommodate intermittent or unreliable links by delaying wireless transmission of data until a link of sufficient strength is established. Such an auto device detection mode may also be desirable in a caregiver office environment to enable the system to download data (automatically or upon patient approval) whenever a patient enters the waiting room. If the auto device detection mode is active (query task 1408), then the translation device may check to determine whether a local device has been detected (query task 1410). If the translation device detects a local device within range, then data storage and translation process 1400 may continue as described below. Otherwise, the translation device may idle until it detects a local device within range, or process 1400 may be re-entered at query task 1408. If the auto device detection mode is inactive, or if the translation device does not support the auto device detection mode, then query task 1408 may lead to a query task 1412.

Data storage and translation process 1400 may perform query task 1412 to determine whether a user of the host application has assumed control over the translation device. If host control is not initiated, then process 1400 may be re-entered at query task 1408. Alternatively, if host control is not initiated, then process 1400 may idle until host control occurs. If, however, host control is initiated, then process 1400 may continue as described below.

Figure 20A:
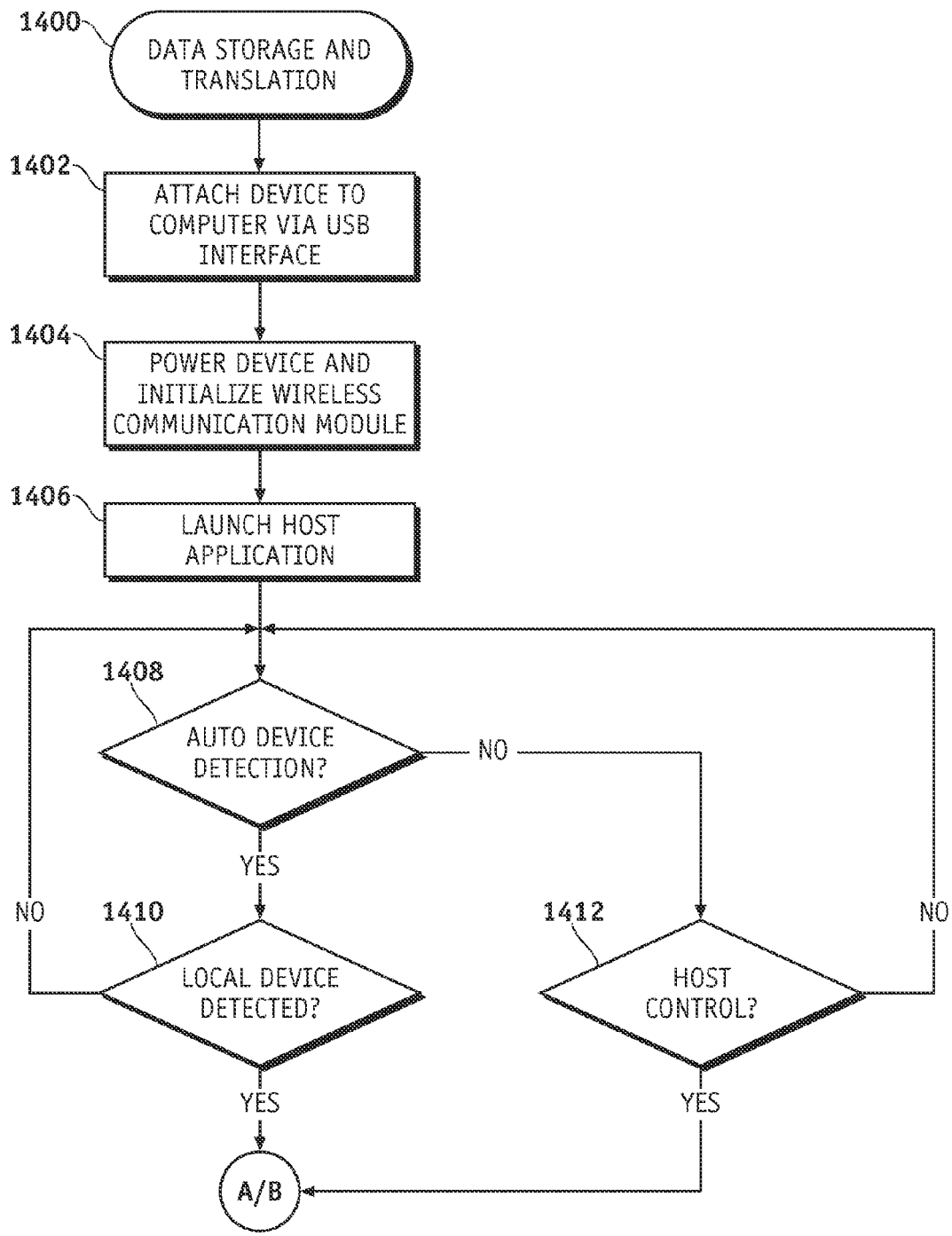
FIG. 20 is a flow chart that depicts an example data storage and translation process.
Figure 20B:
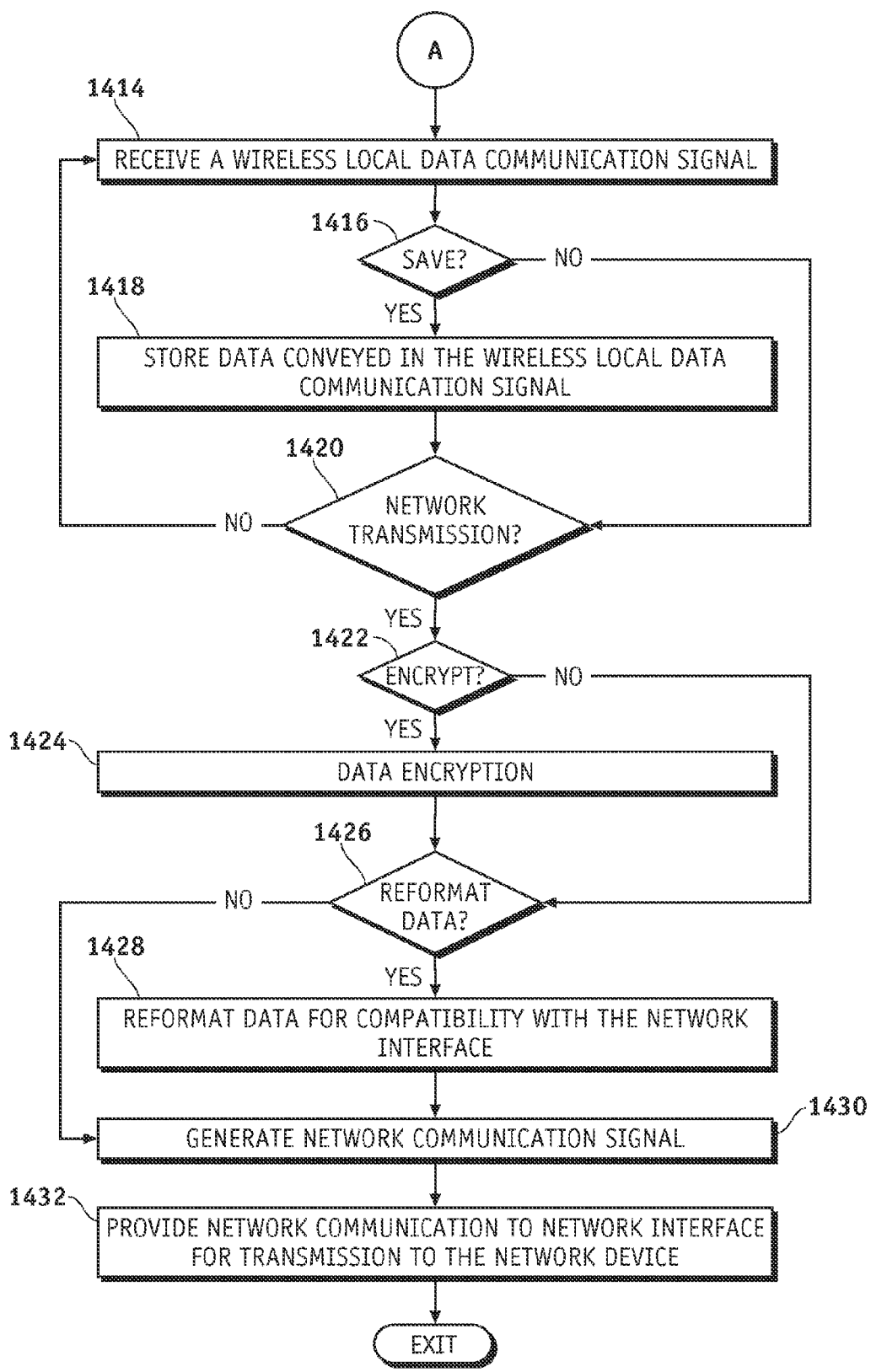
Figure 20C:
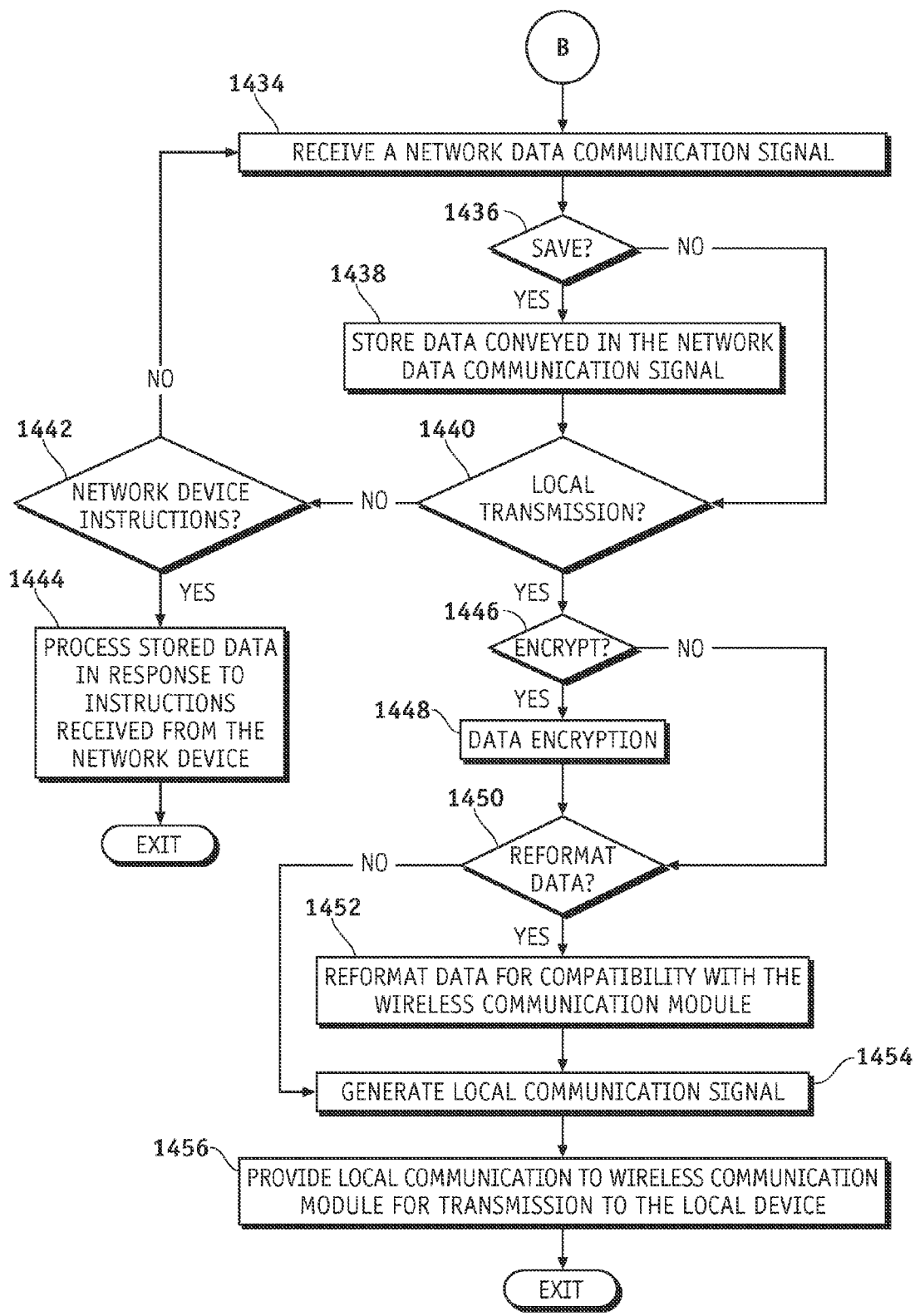

Depending upon the implementation and the application, the translation device may receive and process data from a wireless local device and/or receive and process data from a network device. For ease of description, data storage and translation process 1400 is arbitrarily and artificially separated into sub-process A (relating to the handling of incoming wireless communication signals) and sub-process B (relating to the handling of incoming network communication signals). An embodiment of the translation device may be suitably configured to carry out both sub-processes concurrently or in a synchronous manner that avoids transmit/receive clashes. Either or both of these sub-processes may follow query task 1410 or query task 1412, as indicated in FIG. 20A.

Referring to sub-process A (see FIG. 20B), the translation device may receive a wireless local data communication signal from a local device within the infusion system (task 1414). In one example embodiment, during an initial handshaking or packet exchange routine, the device initiating contact indicates whether the transmission is a one-time packet (which could be sent as often as required) or a synchronous-link packet that requires time synchronization of packets sent and received between the two communicating devices. If data conveyed in the received wireless local data communication signal is to be saved (query task 1416), then the translation device may extract and store the data in its resident memory element (task 1418). Following the data storage of task 1418, data storage and translation process 1400 may proceed to a query task 1420. If data conveyed in the wireless local data communication signal is not to be saved, then process 1400 may bypass task 1418 and proceed to query task 1420.

Query task 1420 may determine whether the translation device is to perform network transmission of data. The translation device may be suitably configured to support network transmission of data stored in the memory element and/or network transmission of data that need not be stored in the memory element. For example, the translation device may be configured to process data stored in the memory element for transmission to a network device that is external to the infusion system. In this example, such network transmission corresponds to transmission of data from the translation device to the host computer via the USB interface. If network transmission has not been initiated, then data storage and translation process 1400 may be re-entered at task 1414 to allow the translation device to continue receiving wireless communication signals. If, however, network transmission has been initiated, then process 1400 may proceed to a query task 1422.

Query task 1422 determines whether the translation device is to perform data encryption. The translation device may be suitably configured to encrypt data conveyed in wireless local data communication signals, to encrypt data conveyed in network communication signals, and/or to encrypt data stored in the memory element. For example, the translation device may encrypt data stored in the memory element for encrypted transmission to the network device, which is compatibly configured to decrypt the data. If encryption is to be performed, then data storage and translation process 1400 performs data encryption (task 1424) using any suitable data encryption technique. After process 1400 performs encryption, it may lead to a query task 1426. If the data will not be encrypted, then process 1400 may bypass task 1424 and proceed to query task 1426.

Query task 1426 determines whether the translation device is to reformat data for transmission to the network device. For example, data storage and translation process 1400 may reformat data conveyed in the wireless local data communication signal for compatibility with the network interface (task 1428). Process 1400 may additionally (or alternatively) reformat data that has been stored in the memory element. Such reformatting may be desirable to enable the network interface to provide network communications to the network device, where the network communications convey the reformatted data. After reformatting data in a desired manner, the translation device can generate a network communication signal (task 1430). Task 1430 may also be performed if query task 1426 determines that reformatting is unnecessary or undesired. In this example, the network communication signal includes data that was conveyed in the wireless local data communication signal and/or data retrieved from the memory element.

Eventually, data storage and translation process 1400 provides the network communication signal (generated during task 1430) to the network interface for transmission to the network device (task 1432). In the example embodiment, task 1432 results in the transmission of data to the host computer via the USB interface. Following task 1432, process 1400 may exit or it may be re-entered at a designated point, such as query task 1408.

Referring to sub-process B (see FIG. 20C), the translation device may receive a network data communication signal from a network device that is external to the infusion system (task 1434). In one example embodiment, during an initial handshaking or packet exchange routine, the device initiating contact indicates whether the transmission is a one-time packet (which could be sent as often as required) or a synchronous-link packet that requires time synchronization of packets sent and received between the two communicating devices. If data conveyed in the network data communication signal is to be saved (query task 1436), then the translation device may extract and store the data in its resident memory element (task 1438). Thereafter, data storage and translation process 1400 may proceed to a query task 1440. If data conveyed in the network data communication signal is not to be saved, then process 1400 may bypass task 1438 and proceed to query task 1440.

Query task 1440 may determine whether the translation device is to perform local transmission of data. The translation device may be suitably configured to support local transmission of data stored in the memory element and/or local transmission of data that need not be stored in the memory element. For example, the translation device may be configured to process data stored in the memory element for transmission to a local device within the infusion system. In this example, such local transmission corresponds to transmission of data from the translation device to a local device via the wireless communication module. If local transmission has not been initiated, then data storage and translation process 1400 may check whether the received network data communication signal conveys operating or control instructions from the network device (query task 1442). If so, then the translation device may process data stored in the memory element in response to such instructions (task 1444). These instructions may include or indicate a request for certain data stored at the translation device, a request for the translation device to obtain data from a local device, programming or configuration data for the translation device and/or a local device, or the like. Following task 1444, process 1400 may exit or it may be re-entered at a designated point, such as task 1434 or query task 1408.

If query task 1440 determines that local transmission has been initiated, then data storage and translation process 1400 may proceed to a query task 1446. Query task 1446 determines whether the translation device is to perform data encryption as described previously. For example, the translation device may encrypt data conveyed in the received network data communication signal and/or data stored in the memory element for encrypted transmission to the wireless local device, which is compatibly configured to decrypt the data. If encryption is to be performed, then process 1400 performs data encryption (task 1448) using any suitable data encryption technique. After process 1400 encrypts the data, it may proceed to a query task 1450. If the data will not be encrypted, then process 1400 may bypass task 1448 and proceed to query task 1450.

Query task 1450 determines whether the translation device is to reformat data for transmission to the wireless local device. For example, data storage and translation process 1400 may reformat data conveyed in the network data communication signal for compatibility with the wireless data communication module (task 1452). Process 1400 may additionally (or alternatively) reformat data that has been stored in the memory element. Such reformatting may be desirable to enable the wireless communication module to provide local wireless communication signals to the local device(s), where the wireless signals convey the reformatted data. After reformatting data in a desired manner, the translation device can generate a local communication signal (task 1454). Task 1454 may also be performed if query task 1450 determines that reformatting is unnecessary or undesired. In this example, the local communication signal is a wireless signal that includes data that was conveyed in the network data communication signal and/or data retrieved from the memory element.

Eventually, data storage and translation process 1400 provides the local communication signal (generated during task 1454) to the wireless communication module for transmission to the local device (task 1456). In the example embodiment, task 1456 results in the wireless transmission of data to a local device via the wireless communication module. Following task 1456, process 1400 may exit or it may be re-entered at a designated point, such as query task 1408.

Translation device 1300, data storage and translation process 1400, and other processes supported by translation device 1300 provide added flexibility and convenience for users of the infusion system. For example, translation device 1300 can support the downloading of history data from an infusion pump or an infusion pump monitor with automatic storage to its internal flash memory. Such downloading may be driven by the host application—the host computer can command translation device 1300 to download data to the flash memory—for retrieval and analysis at a later date by the patient's caregiver. Patient history data may be encrypted such that only an authorized caregiver computer system can access the history files. Alternatively, the history files could be read-only by the patient, with read/write access provided to the caregiver. In example embodiments, the host application may be configured to detect whether the patient or a caregiver is communicating with the local device via translation device 1300. Consequently, translation device 1300 may be configured to support patient-specific and/or caregiver-specific functions and operations if so desired.

Figure 21:
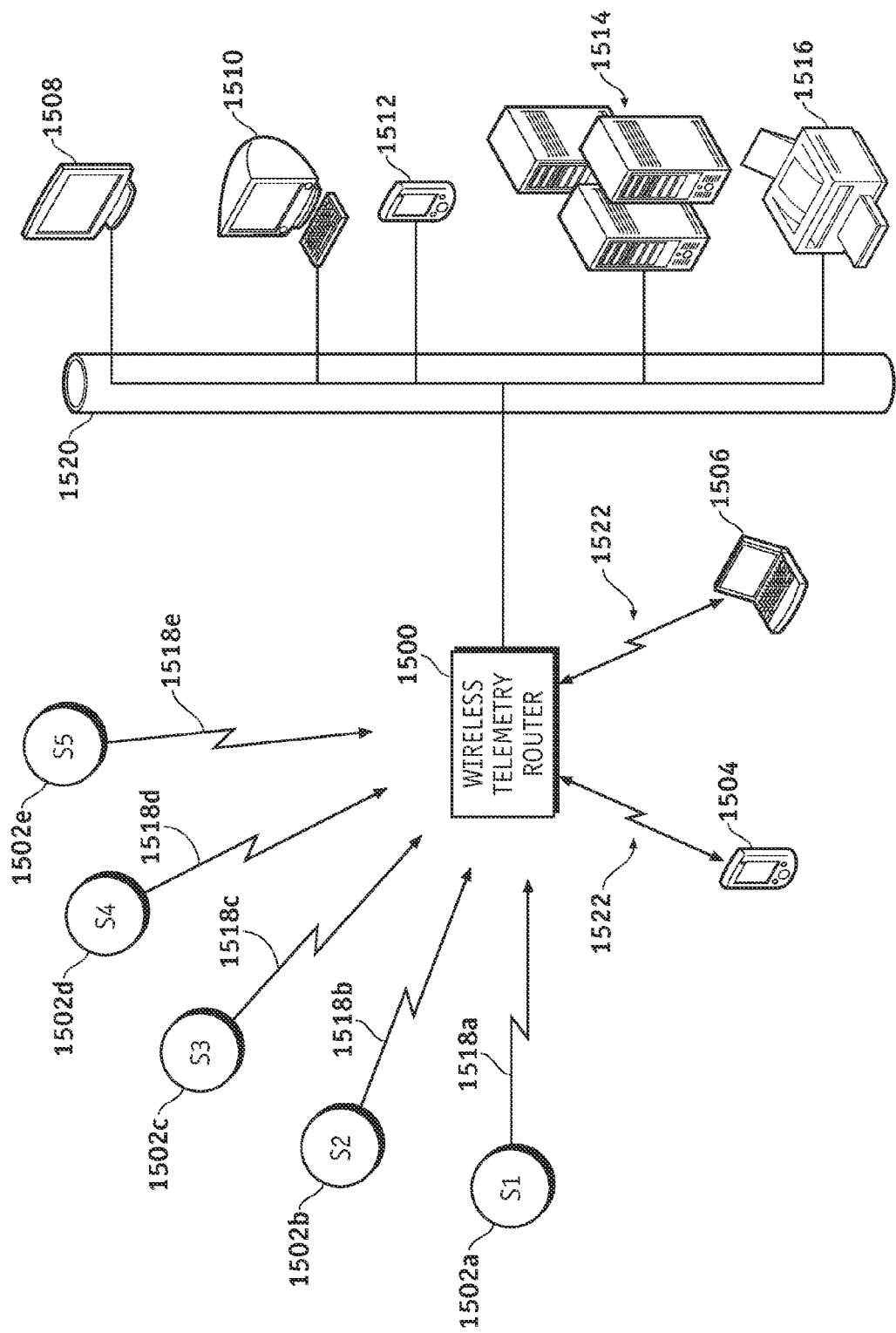
FIG. 21 is a schematic representation of an example network deployment of a wireless telemetry router configured in accordance with an example embodiment of the invention.

Depending upon the given deployment of an infusion system, it may be desirable to collect data from a plurality of local devices such that the collected data can be stored, processed, routed, or otherwise managed in an controlled manner. In this regard, FIG. 21 is a schematic representation of an example network deployment of a wireless telemetry router 1500 configured in accordance with an example embodiment of the invention. Wireless telemetry router 1500 may be deployed in a medical device system such as network-based infusion system 100 (see FIG. 1). Wireless telemetry router 1500 is suitably configured to communicate with a plurality of wireless devices within a local medical device system, such as a local infusion system. Wireless telemetry router 1500 is also configured to communicate with one or more network devices, which may be external to the local medical device system. For example, wireless telemetry router 1500 may communicate with network devices coupled to wireless telemetry router 1500 via an Ethernet connection and/or via wireless links.

The flexible nature of the example environment is depicted in FIG. 21, which depicts wireless telemetry router 1500 in communication with a variety of devices. In an example embodiment, wireless telemetry router 1500 may be suitably configured to communicate with one or more of the following devices, without limitation: a plurality of physiological characteristic sensor transmitters 1502, a wireless personal digital assistant 1504, a wireless laptop computer 1506, a network monitor 1508, a network computer 1510, a network personal digital assistant 1512, a network hospital management system 1514, and a network printer 1516. Wireless telemetry router 1500 may also be configured to support communication with the various local devices and network devices mentioned in the above description of infusion system 100.

Although FIG. 21 depicts five physiological characteristic sensor transmitters 1502, wireless telemetry router 1500 can support any number of sensor transmitters (limited only by practical operating restrictions such as bandwidth, available power, transmission range, etc.). Each physiological characteristic sensor transmitter 1502 is suitably configured to measure a physiologic characteristic of a patient. In the example infusion system described here, each sensor transmitter 1502 is a continuous glucose (e.g., blood glucose) sensor transmitter that measures the glucose level of a patient in real time. Each sensor transmitter 1502 may be realized in a form that is intended to be worn by the patient, attached to the patient's skin, implanted within the patient's body, or the like. Each sensor transmitter 1502 includes a wireless transmitter that facilitates transmission of physiologic sensor data of the user to wireless telemetry router 1500 and possibly other devices within the local infusion system.

Wireless telemetry router 1500 may be deployed in any environment where physiological characteristic sensor transmitters 1502 might come in range. Wireless telemetry router 1500 can support a system where a plurality of sensor transmitters 1502 are used by one person and/or a system that contemplates more than one person (each using only one sensor transmitter 1502). Moreover, wireless telemetry router 1500 can be suitably configured to support different types of sensor transmitters, and the example environment depicted in FIG. 21 need not be limited to an insulin infusion system or any specific type of medical device system. Example applications of wireless telemetry router 1500 include the following, without limitation: one patient having multiple sensor transmitters 1502, each being configured to provide data indicative of a different physiologic characteristic; a home deployment where more than one member of a family uses a sensor transmitter 1502; a school deployment where it may be desirable to monitor the physiologic data for any number of students; a hospital deployment where it may be desirable to monitor physiologic data for any number of patients; or a caregiver office environment where it may be desirable to identify specific sensor transmitters 1502 for purposes of patient identification and/or to obtain data from sensor transmitters 1502.

Physiological characteristic sensor transmitters 1502 and wireless telemetry router 1500 are suitably configured to support wireless data communication via respective wireless links 1518, which may be unidirectional (as shown) or bidirectional, depending upon the particular system and/or the specific type of sensor transmitters 1502. Accordingly, wireless telemetry router 1500 includes a suitably configured wireless communication module that is capable of supporting multiple sensor transmitters 1502.

Although not a requirement of the system, wireless links 1518 may be established using the same wireless data communication protocol and wireless data transmission scheme. Wireless telemetry router 1500 may utilize any number of suitable wireless data communication protocols, techniques, or methodologies for wireless links 1518, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. In the example embodiment, wireless links 1518 are carried over the 900-930 MHz band that is reserved for industrial, scientific, and medical equipment use. As another example, wireless links 1518 in a hospital implementation may utilize the WMTS bands that are reserved for hospital applications. Packaging of sensor data, error detection, security, sensor transmitter identification, and other sensor data processing techniques may be governed by known or proprietary protocols.

Wireless telemetry router 1500 may be configured to communicate with network devices via Ethernet connectivity (or via any suitable data communication methodology). FIG. 21 depicts an Ethernet data communication architecture 1520 that links wireless telemetry router 1500 to network monitor 1508, network computer 1510, network personal digital assistant 1512, network hospital management system 1514, and network printer 1516. Of course, these example network devices are not exhaustive, and embodiments of the invention are not limited to these examples. A given link between wireless telemetry router 1500 and a network device may be unidirectional (in either direction) or bidirectional, depending upon the particular system and/or the specific type of network device. For example, the link from wireless telemetry router 1500 to network printer 1516 may be unidirectional, the link from wireless telemetry router 1500 to network monitor 1508 may be unidirectional, and other links may be bidirectional.

Wireless telemetry router 1500 may be configured to support wireless communication with compatible wireless devices, such as wireless personal digital assistant 1504 and wireless laptop computer 1506. Accordingly, wireless telemetry router 1500 includes a suitably configured wireless communication module, which may (but need not) be distinct from the wireless communication module that receives wireless links 1518. In this regard, FIG. 21 depicts wireless links 1522 between wireless telemetry router 1500 and these wireless devices. A given wireless link 1522 between wireless telemetry router and a wireless device may be unidirectional in either direction or bidirectional (as shown in FIG. 21), depending upon the particular system and/or the specific type of wireless device. In practice, wireless links 1522 enable wireless telemetry router 1500 to communicate directly with wireless devices while bypassing the network (i.e., without having to traverse Ethernet data communication architecture 1520).

Although not a requirement of the system, wireless links 1522 may be established using the same wireless data communication protocol and wireless data transmission scheme. In this example, wireless telemetry router 1500 utilizes one wireless data communication technique for wireless links 1522 and a different wireless data communication technique for wireless links 1518. Wireless telemetry router 1500 may utilize any number of suitable wireless data communication protocols, techniques, or methodologies for wireless links 1522, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Packaging of data, error detection, security, and other data processing techniques may be governed by known or proprietary protocols.

In one example embodiment, wireless telemetry router 1500 includes an HTML-based setup, management, and control interface that can be accessed via any authorized computer or device having HTML browser capabilities and connectivity to wireless telemetry router 1500. For example, an administrator may be able to access wireless telemetry router 1500 via the Internet and a conventional web browser application residing on wireless personal digital assistant 1504, wireless laptop computer 1506, network computer 1510, or network personal digital assistant 1512. The control interface may be provided as one or more HTML pages that reside in the firmware/software of wireless telemetry router 1500. The control interface can be accessed using an IP address and/or a network interface card that is unique to that particular wireless telemetry router 1500. Password and firewall protection may be implemented to provide protection against external misuse or data theft.

In connection with a setup procedure, wireless telemetry router 1500 may be provided with sensor identifiers for the respective physiological characteristic sensor transmitters 1502. The sensor identifiers may be, for example, the serial numbers of sensor transmitters 1502 or any information that uniquely distinguishes the different sensor transmitters 1502 within the operating environment. In example embodiments, wireless communication signals generated by an originating sensor transmitter 1502 conveys the corresponding sensor identifier. Wireless telemetry router 1500 can then process the sensor identifiers in a suitable manner. For example, wireless telemetry router 1500 may receive a wireless communication signal from an originating sensor transmitter 1502, obtain or extract the sensor identifier for that wireless communication signal, and process the sensor data conveyed in that wireless communication signal in a manner that is determined, governed, or dictated by the particular sensor identifier. This technique enables wireless telemetry router 1500 to identify the originating sensor transmitter 1502, the originating patient, the sensor transmitter type, or other pertinent information. Wireless telemetry router 1500 may then process, store, and/or route the sensor data in an appropriate manner. As another example, wireless telemetry router 1500 may receive a first wireless communication signal from a first sensor transmitter 1502*a*, receive a second wireless communication signal from a second sensor transmitter 1502*b*, obtain or extract the two respective sensor identifiers (which should be different), and process the sensor data conveyed in the two wireless communication signals in a synchronized manner that is determined, governed, or dictated by the sensor identifiers. This technique enables wireless telemetry router 1500 to prioritize the receipt, processing, storage, and/or transmission of sensor data depending upon the originating source.

In connection with a setup procedure, wireless telemetry router 1500 may be provided with network identifiers (e.g., IP addresses or network interface card identifiers) for the various destination network devices. Such network identifiers enable wireless telemetry router 1500 to determine how to process, handle, store, or route the received sensor data. In this regard, wireless telemetry router 1500 may, for example, maintain or access a lookup table (or any suitable memory or database structure) that contains the different sensor identifiers and a corresponding list of destination network identifiers for each sensor identifier. This lookup table may also include corresponding processing instructions for each sensor identifier.

Wireless telemetry router 1500 is generally configured to receive sensor data and route the sensor data to one or more destination network devices. In this example, wireless telemetry router 1500 receives a plurality of wireless communication signals from a plurality of physiological characteristic sensor transmitters 1502, where each wireless communication signal conveys sensor data generated by a respective sensor transmitter 1502. As mentioned above, each wireless communication signal may also convey a sensor identifier that uniquely identifies the originating sensor transmitter 1502. Wireless telemetry router 1500 can then process the received information in an appropriate manner, depending upon the particular application and the identity of the originating sensor transmitter 1502.

Wireless telemetry router 1500 may perform one or more operations on the received sensor data, including, without limitation: storing at least some of the sensor data (at wireless telemetry router 1500 itself or at a network device that is coupled to wireless telemetry router 1500); forward at least some of the sensor data to a destination network device; reformat data conveyed in the wireless communication signals for compatibility with a designated network data communication protocol; or process at least some of the sensor data. In example embodiments, wireless telemetry router 1500 may include some functionality and processing intelligence that might normally be found elsewhere in the system environment. For example, wireless telemetry router 1500 may be configured to receive uncalibrated physiologic characteristic data, such as an uncalibrated patient glucose level, and calibrate the data before routing it to the destination network device.

In connection with its routing function, wireless telemetry router 1500 may generate a network communication that complies with a specified network data communication protocol. The network communication conveys sensor data, which may include stored sensor data, real-time sensor data that is being immediately routed, or a combination thereof Wireless telemetry router 1500 can then transmit the network communication to one or more network devices. Wireless telemetry router 1500 transmits the network communication in accordance with the selected network data communication protocol and in accordance with the selected data transmission technique. For example, wireless telemetry router 1500 may function as a translation device between data received on wireless links 1518 (using one protocol and transmission scheme combination) and data transmitted over Ethernet data communication architecture 1520 (using another protocol and transmission scheme combination). As another example, wireless telemetry router 1500 may function as a translation device between data received on wireless links 1518 (using one protocol and transmission scheme combination) and data transmitted over wireless links 1522 (using another protocol and transmission scheme combination).

Wireless telemetry router 1500 may also be configured to generate warning, error, alarm, and alert information ("diagnostic information"), which may be routed using the techniques described above. The diagnostic information may be displayed or rendered at wireless telemetry router 1500 itself and/or routed for display or rendering at a network device. The diagnostic information may include, without limitation: information related to the operation or status of wireless telemetry router 1500; information related to the operation or status of physiological characteristic sensor transmitters 1502; information related to the operation or status of a network device; or any of the notifications, alerts, alarms, or status reports described in more detail above.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention, where the scope of the invention is defined by the claims, which includes known equivalents and foreseeable equivalents at the time of filing this patent application.

What is claimed is:

1. A method for remote monitoring and operating of an external infusion pump that is part of a local infusion system, the infusion pump controlling the infusion of fluid into the body of a user via an infusion set having a cannula inserted under the skin of the user, the method comprising:
   receiving, at a network device that is external to the infusion system, a network communication generated by a transmitting device within the infusion system, the network communication conveying pump data associated with the infusion pump, wherein the transmitting device is one of a plurality of different local devices in the local infusion system;
   extracting the pump data from the network communication;
   processing the pump data to generate an activation instruction to remotely activate delivery of fluid by the infusion pump;
   selecting one of the plurality of different local devices as an intended recipient device for the activation instruction;
   selecting, from a plurality of data communication protocols, one or more protocols corresponding to the intended recipient device, wherein the selected one or more protocols facilitate compatible communication with the intended recipient device; and
   transmitting the activation instruction in a network control communication that is intended for the infusion pump, wherein the network control communication is transmitted in accordance with the selected one or more protocols, and wherein the activation instruction causes the infusion pump to deliver fluid to the body of the user in accordance with the activation instruction.

2. The method of claim 1, further comprising the step of generating, at the network device, indicia of the pump data.

3. The method of claim 2, the pump data including status information of the transmitting device, and the generating step comprising generating indicia of the status information.

4. The method of claim 2, the pump data including status information of the infusion pump, and the generating step comprising generating indicia of the status information.

5. The method of claim 2, the pump data including an alert related to operation of the transmitting device, and the generating step comprising generating indicia of the alert.

6. The method of claim 5, further comprising:
   generating, at the network device, an alert enable or disable instruction for the transmitting device; and
   transmitting a control communication to the transmitting device, the control communication conveying the alert enable or disable instruction.

7. The method of claim 2, the pump data including a basal rate of fluid delivered to the user by the infusion pump, and the generating step comprising generating indicia of the basal rate.

8. The method of claim 2, the pump data including bolus information for a bolus of fluid delivered to the user by the infusion pump, and the generating step comprising generating indicia of the bolus information.

9. The method of claim 2, wherein generating indicia comprises generating an audible representation of the pump data.

10. The method of claim 2, wherein generating indicia comprises generating a visual representation of the pump data.

11. The method of claim 1, wherein:
   the transmitting device comprises a physiological characteristic meter of the infusion system; and
   the pump data originates at the infusion pump.

12. The method of claim 1, wherein:
   the transmitting device comprises a remote controller for the infusion pump; and
   the pump data originates at the infusion pump.

13. The method of claim 1, wherein:
the transmitting device comprises a handheld monitor/controller for the infusion pump; and
the pump data originates at the infusion pump.

14. The method of claim 1, wherein:
the transmitting device comprises a monitor device for the infusion pump; and
the pump data originates at the infusion pump.

15. The method of claim 1, further comprising:
generating, at the network device, a programming parameter for the infusion pump; and
transmitting a control communication to the infusion pump, the control communication conveying the programming parameter.

\* \* \* \* \*